United States Patent
Paradis

[19]
[11] Patent Number: 6,068,011
[45] Date of Patent: *May 30, 2000

[54] CONTROL OF FLUID FLOW

[76] Inventor: Joseph R. Paradis, 17 Hickory Forest Dr., Hilton Head Island, S.C. 29926

[*] Notice: This patent is subject to a terminal disclaimer.

[21] Appl. No.: 08/955,652

[22] Filed: Oct. 22, 1997

Related U.S. Application Data

[63] Continuation of application No. 08/290,136, Aug. 15, 1994, Pat. No. 5,699,821, which is a continuation-in-part of application No. 08/135,673, Oct. 13, 1993, Pat. No. 5,509,433.

[51] Int. Cl.$^7$ .................................................... A61M 5/00
[52] U.S. Cl. .................. 137/1; 251/149.1; 251/149.6; 604/167; 604/256; 604/905
[58] Field of Search ............................. 251/149.1, 149.8, 251/149.6; 604/167, 256, 83, 905, 283, 249; 137/1

[56] References Cited

U.S. PATENT DOCUMENTS

| | | |
|---|---|---|
| 34,894 | 4/1862 | Lynde . |
| 932,146 | 8/1909 | Lebold et al. . |
| 3,352,531 | 11/1967 | Kilmarx . |
| 3,389,839 | 6/1968 | Williams et al. . |
| 3,585,984 | 6/1971 | Buchanan . |
| 3,620,500 | 11/1971 | Santomieri . |
| 3,734,080 | 5/1973 | Petterson . |
| 3,831,629 | 8/1974 | Mackal et al. ............... 137/903 X |
| 3,837,381 | 9/1974 | Arroyo . |
| 3,977,400 | 8/1976 | Moorehead . |
| 3,986,508 | 10/1976 | Barrington . |
| 4,143,853 | 3/1979 | Abramson . |
| 4,387,879 | 6/1983 | Tauschinski . |
| 4,425,122 | 1/1984 | Cohen . |
| 4,429,856 | 2/1984 | Jackson . |
| 4,496,348 | 1/1985 | Genese et al. . |
| 4,512,766 | 4/1985 | Vailancourt . |
| 4,673,400 | 6/1987 | Martin . |
| 4,710,168 | 12/1987 | Schwab et al. . |

(List continued on next page.)

FOREIGN PATENT DOCUMENTS

| | | |
|---|---|---|
| 1104991 | 7/1981 | Canada . |
| 1183749 | 3/1985 | Canada . |
| 1203823 | 4/1986 | Canada . |

(List continued on next page.)

OTHER PUBLICATIONS

Check Valve, Nypro, Inc., 1986.

"Needlestick–prevention Devices for IV Therapy and IM and Subcutaneous Medication Administration", Health Devices, Aug.–Sep. 1994, vol. 23, Nos. 809, pp. 316–345.

Skousen, Philip L. *Valve Handbook*. McGraw–Hill: 1998. pp. V–viii (Table of Contents).

*Valves, Piping & Pipelines Handbook*. (Elsevier Advanced Technology: 1994) pp. 69–79.

(List continued on next page.)

*Primary Examiner*—Kevin Lee
*Attorney, Agent, or Firm*—Morgan & Finnegan, LLP

[57] ABSTRACT

A flow control device has an inlet, an outlet and a conduit connecting the inlet to the outlet enabling fluid flow from the inlet to the outlet. A movable head with a slot therethrough seals the inlet. The head is connected to elongated legs which are flexed when the head is moved out of the inlet, opening the slot, providing a return force for returning the head to its position sealing the inlet. Preferably, the slot is normally open and the inlet closes the slot when the head is in the inlet. Movement of the head out of the inlet opens the slot, permitting the passage of fluid through the head. A spring can bias the head toward the inlet, instead of the elongated legs. A member external to the flow control device, such as the tip of a Luer taper, can open the slot by depressing the head, allowing the flow of fluid through the device.

47 Claims, 19 Drawing Sheets

U.S. PATENT DOCUMENTS

| | | |
|---|---|---|
| 4,752,292 | 6/1988 | Lopez et al. . |
| 4,782,841 | 11/1988 | Lopez . |
| 4,895,346 | 1/1990 | Steigerwald . |
| 4,915,687 | 4/1990 | Sivert . |
| 4,946,448 | 8/1990 | Richmond . |
| 5,006,114 | 4/1991 | Rogers et al. . |
| 5,024,616 | 6/1991 | Ogle, II . |
| 5,060,812 | 10/1991 | Ogle, II . |
| 5,062,836 | 11/1991 | Wendell . |
| 5,064,416 | 11/1991 | Newgard et al. . |
| 5,074,312 | 12/1991 | Sarstedt . |
| 5,085,645 | 2/1992 | Purdy et al. . |
| 5,108,380 | 4/1992 | Herlitz et al. . |
| 5,147,333 | 9/1992 | Raines . |
| 5,163,922 | 11/1992 | McElveen, Jr. et al. . |
| 5,199,947 | 4/1993 | Lopez et al. . |
| 5,201,725 | 4/1993 | Kling . |
| 5,203,775 | 4/1993 | Frank et al. ........ 604/283 X |
| 5,242,393 | 9/1993 | Brimhall et al. ........ 604/283 X |
| 5,242,432 | 9/1993 | DeFrank . |
| 5,269,771 | 12/1993 | Thomas et al. ........ 251/149.1 X |
| 5,273,533 | 12/1993 | Bonaldo . |
| 5,280,876 | 1/1994 | Atkins . |
| 5,295,658 | 3/1994 | Atkinson et al. . |
| 5,300,034 | 4/1994 | Behnke et al. . |
| 5,306,243 | 4/1994 | Bonaldo . |
| 5,322,516 | 6/1994 | Brugger . |
| 5,322,518 | 6/1994 | Schneider et al. . |
| 5,338,313 | 8/1994 | Mollenauer et al. . |
| 5,354,275 | 10/1994 | Behnke et al. . |
| 5,360,413 | 11/1994 | Leason et al. . |
| 5,380,306 | 1/1995 | Brinon . |
| 5,389,086 | 2/1995 | Attermeier et al. . |
| 5,405,331 | 4/1995 | Behnke et al. . |
| 5,453,089 | 9/1995 | Brugger . |
| 5,470,319 | 11/1995 | Mayer ........ 604/167 |
| 5,474,536 | 12/1995 | Bonaldo . |
| 5,474,544 | 12/1995 | Lynn . |
| 5,487,728 | 1/1996 | Vaillancourt . |
| 5,514,109 | 5/1996 | Mollenauer et al. . |
| 5,549,566 | 8/1996 | Elias et al. ........ 604/167 |
| 5,549,577 | 8/1996 | Siegel et al. . |
| 5,556,387 | 9/1996 | Mollenauer et al. . |
| 5,685,866 | 11/1997 | Lopez . |
| 5,694,686 | 12/1997 | Lopez . |
| 5,699,821 | 12/1997 | Paradis ........ 251/149.1 X |
| 5,814,024 | 9/1998 | Thompson et al. ........ 304/256 X |

FOREIGN PATENT DOCUMENTS

| | | |
|---|---|---|
| 1268680 | 5/1990 | Canada . |
| 1269866 | 6/1990 | Canada . |
| 2271790 | 7/1990 | Canada . |
| 2049044 | 10/1990 | Canada . |
| 2043343 | 2/1992 | Canada . |
| 2089750 | 3/1992 | Canada . |
| 2119742 | 4/1993 | Canada . |
| 2120947 | 4/1993 | Canada . |
| 2141852 | 2/1994 | Canada . |
| 2150917 | 6/1994 | Canada . |
| 0 150 666 | 8/1985 | European Pat. Off. . |
| 0 157 906 B1 | 10/1985 | European Pat. Off. . |
| 0 159 041 B1 | 10/1985 | European Pat. Off. . |
| 0 159 260 A1 | 10/1985 | European Pat. Off. . |
| 0 210 432 | 2/1987 | European Pat. Off. . |
| 0 271 358 A2 | 6/1988 | European Pat. Off. . |
| 0 276 556 B1 | 8/1988 | European Pat. Off. . |
| 0309771 | 9/1988 | European Pat. Off. . |
| 0 287 289 B1 | 10/1988 | European Pat. Off. . |
| 0 309 771 B1 | 4/1989 | European Pat. Off. . |
| 0 316 096 B1 | 5/1989 | European Pat. Off. . |
| 0 329 660 B1 | 5/1989 | European Pat. Off. . |
| 0 336 307 A2 | 10/1989 | European Pat. Off. . |
| 0 346 785 B1 | 12/1989 | European Pat. Off. . |
| 0 415 691 B1 | 3/1991 | European Pat. Off. . |
| 0 471 547 A1 | 2/1992 | European Pat. Off. . |
| 0 472 088 A1 | 2/1992 | European Pat. Off. . |
| 0 477 239 B1 | 4/1992 | European Pat. Off. . |
| 0 511 538 A2 | 11/1992 | European Pat. Off. . |
| 0 544 654 B1 | 6/1993 | European Pat. Off. . |
| 0 546 223 B1 | 6/1993 | European Pat. Off. . |
| 0 550 069 A1 | 7/1993 | European Pat. Off. . |
| 0 560 221 B1 | 9/1993 | European Pat. Off. . |
| 0 563 357 B1 | 10/1993 | European Pat. Off. . |
| 0 567 202 B1 | 10/1993 | European Pat. Off. . |
| 2049513 | 3/1971 | France . |
| 2058579 | 5/1971 | France . |
| 2065031 | 7/1971 | France . |
| 2103112 | 4/1972 | France . |
| 2125696 | 9/1972 | France . |
| 2316970 | 2/1977 | France . |
| 2343487 | 10/1977 | France . |
| 2393583 | 1/1979 | France . |
| 2413913 | 8/1979 | France . |
| 2455900 | 12/1980 | France . |
| 2475903 | 8/1981 | France . |
| 2642499 | 8/1990 | France . |
| 2666745 | 3/1992 | France . |
| 2 106 266 | 9/1972 | Germany . |
| 26 27 439 | 12/1976 | Germany . |
| 26 23 511 | 2/1977 | Germany . |
| 28 17 102 | 10/1979 | Germany . |
| 30 06 291 | 8/1980 | Germany . |
| 31 00 622 A1 | 2/1982 | Germany . |
| 30 31 242 | 3/1982 | Germany . |
| 31 16 427 | 3/1982 | Germany . |
| 30 42 229 A1 | 5/1982 | Germany . |
| 30 48 203 | 7/1982 | Germany . |
| 31 00 442 C1 | 9/1982 | Germany . |
| 31 32 323 A1 | 4/1983 | Germany . |
| 32 10 148 A1 | 9/1983 | Germany . |
| 32 42 238 A1 | 5/1984 | Germany . |
| 33 03 073 C1 | 9/1984 | Germany . |
| 3303718 C1 | 10/1984 | Germany . |
| 33 30 149 A1 | 3/1985 | Germany . |
| 35 37 341 A1 | 4/1987 | Germany . |
| 37 32 515 A1 | 4/1989 | Germany . |
| 38 09 127 C1 | 4/1989 | Germany . |
| 39 13 392 A1 | 10/1990 | Germany . |
| 40 26 524 A1 | 3/1992 | Germany . |
| 41 00 591 A1 | 7/1992 | Germany . |
| 42 14 783 A1 | 9/1993 | Germany . |
| 42 20 647 A1 | 1/1994 | Germany . |
| 43 04 949 A1 | 8/1994 | Germany . |
| 44 32 993 C1 | 6/1996 | Germany . |
| 61-21107 | 5/1986 | Japan . |
| 4-502570 | 5/1992 | Japan . |
| 4-503179 | 6/1992 | Japan . |
| 67817 | 12/1913 | Switzerland . |
| 636526 | 12/1978 | Switzerland . |
| 498438 | 5/1976 | U.S.S.R. . |
| 572181 | 7/1977 | U.S.S.R. . |
| 752086 | 9/1980 | U.S.S.R. . |
| 1091846 | 5/1984 | U.S.S.R. . |
| 1296171 A1 | 3/1987 | U.S.S.R. . |
| 1532054 A1 | 12/1989 | U.S.S.R. . |
| 1572647 A2 | 6/1990 | U.S.S.R. . |
| 1801506 A1 | 3/1993 | U.S.S.R. . |
| 1812996 A3 | 4/1993 | U.S.S.R. . |
| 1192986 | 5/1970 | United Kingdom . |
| 1277377 | 6/1972 | United Kingdom . |
| 1297794 | 11/1972 | United Kingdom . |
| 1313030 | 4/1973 | United Kingdom . |

| | | |
|---|---|---|
| 1 345 979 | 2/1974 | United Kingdom . |
| 1345980 | 2/1974 | United Kingdom . |
| 1348794 | 3/1974 | United Kingdom . |
| 1411863 | 10/1975 | United Kingdom . |
| 1514920 | 9/1978 | United Kingdom . |
| 1529742 | 10/1978 | United Kingdom . |
| 1540881 | 2/1979 | United Kingdom . |
| 2067075 | 7/1981 | United Kingdom . |
| 2105003 | 3/1983 | United Kingdom . |
| 2151737 | 7/1985 | United Kingdom . |
| 2190981 | 2/1987 | United Kingdom . |
| 2194311 | 2/1988 | United Kingdom . |
| 2199391 | 6/1988 | United Kingdom . |
| 2213458 | 8/1989 | United Kingdom . |
| 2270725 | 3/1994 | United Kingdom . |
| WO 83/02395 | 7/1983 | WIPO . |
| WO 89/06553 | 7/1989 | WIPO . |
| WO 90/11103 | 10/1990 | WIPO . |
| WO 92/20944 | 11/1992 | WIPO . |
| 9311828 | 6/1993 | WIPO . |
| WO 93/11696 | 6/1993 | WIPO . |
| WO 94/13987 | 6/1994 | WIPO . |
| WO 95/23002 | 8/1995 | WIPO . |
| WO 95/35125 | 12/1995 | WIPO . |
| WO 97/24548 | 7/1997 | WIPO . |

OTHER PUBLICATIONS

"New Products", *Journal of Medical Engineering & Technology*. May/Jun., 1993. pp. 128–130.

Rutowski, J. "A Needleless Intravenous System: An Effective Risk Management Strategy", *Infection Control and Hospital Epidemiology*. Apr., 1993. P 26.

Skolnick, R.; LaRocca, J.; Barba, D. & Paicius, L. "Evaluation and implementation of a needleless intravenous system: Making needlesticks a needless problem", *American Journal of Infection Control*. Feb., 1993. pp. 39–41.

Nakano, K.; Watanabe, J. & Guo, "Experimental Study For the Compensation of Axial Flow Force in a Spool Valve", *Journal of Fluid Control–Fluid Control, Hydraulics & Pneumatics Instrumentation and Fluidics*. vol. 21. Nos. 2–3. 1992. pp. 7–26.

Watton, J. "The Design of a Single–Stage Relief Valve with Directional Damping", *The Journal of Fluid Control–Fluid Control, Hydraulics and Pneumatics, Instrumentation and Fluidics* vol. 18 No. 2 Mar., 1988. pp. 22–35.

Cowell, T.K. "A standard pressure source for calibrating physiological pressure transducers", *Journal of Medical Engineering & Technology*. Jul./Aug., 1986. pp. 201–204.

Hickey, Donald D. "A simple device for the direct measurement of mean arterial pressure and for calibration of arterial pressure monitors", *Journal of Medical Engineering & Technology*. Jul./Aug., 1986. pp. 188–192.

"Evaluation Report: Infusion pumps", *Journal of Medical Engineering & Technology*. May/Jun. 1986. pp. 135–140.

Legallet, J. E. "A Linear Actuator For Valve Control". Thesis, Department of Mechanical Engineering, Massachusetts Institute of Technology. May, 1985.

Kajiya, F.; Tomonaga, G.; Tsujioka, K; Ogasawara, Y. & Nishihara, H. Evaluation of Local.

Blood Flow Velocity in Proximal and Distal Coronary Arteries by Laser Doppler Method, *Journal of Biomechanical Engineering*. vol. 107. Feb., 1985. pp. 10–15.

Feehan, J.P. "A Fail–Safe, Three Way, Variable Flow Control Valve For A Commercially Available, Implantable Insulin Infusion Pump". Thesis, Department of Mechanical Engineering, Massachusetts Institute of Technology. Feb., 1985.

"Evaluation of infusion pumps: third report—volumetric pumps", *Journal of Medical Engineering & Technology*. May/Jun., 1984. pp. 127–132.

"Evaluation of infusion pumps and controllers: fourth report", *Journal of Medical Engineering & Technology*. Nov./Dec., 1984. pp. 277–281.

Cook, Dexter T. "Selecting hand–operated valves for process plants". *The Chemical Engineering Guide to Valves*. Greene, Richard W., editor. (McGraw–Hill, NY, 1984) (article originally published in Jun., 1982). pp. 217–230.

Kern, Robert. "Pressure–relief valves for process plants". *The Chemical Engineering Guide to Valves*. Greene, Richard W., editor. (McGraw–Hill, NY, 1984) (article originally published in Feb., 1977). pp. 92–99.

*Intravenous Therapy Supplies And Equipment Market In Europe*. (Frost & Sullivan, 1983). pp. i–v, 314–317. (Table of Contents & Index).

Schweitzer, Philip A. *Handbook of Valves*. (Robert E. Krieger Publishing Co., 1982). pp. 124–135.

Zappe, R.W. *Valve Selection Handbook*. (Gulf Publishing Co., 1981). p. 2.

Pearson, G.H. *Valve Design*. (Priory Press, London, 1978). P 139.

Lyons, J.L. & Askland, C.L. *Lyon's Encyclopedia of Valves*. (Van Nostrand Reinhold Co., NY, 1975). pp. 3–11, 21, 28, 32, & 50.

Beard, Chester S. *Final Control Elements (Valves & Actuators)*. (Chilton Co., Pennsylvania, 1969). pp. 5–26.

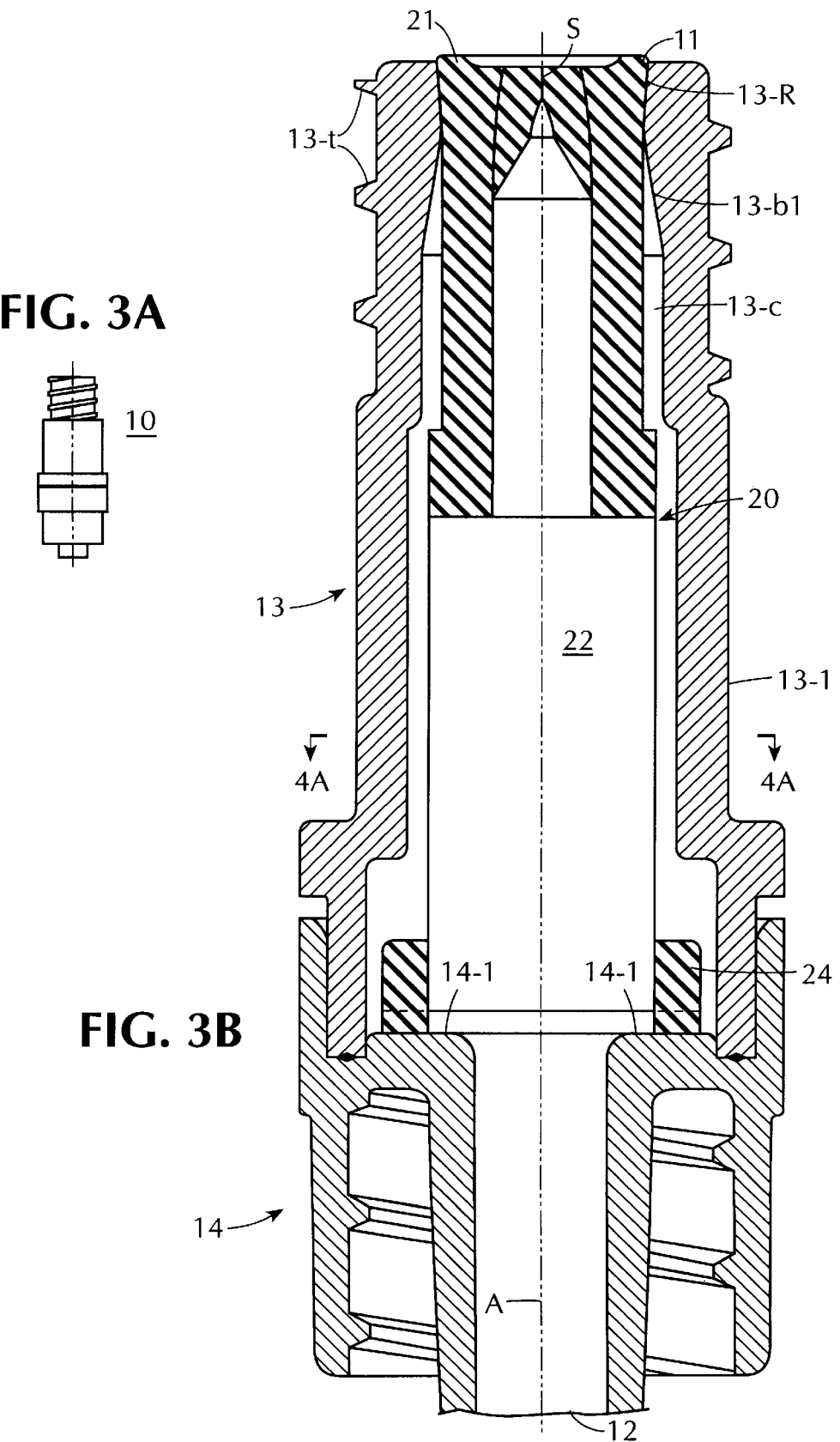

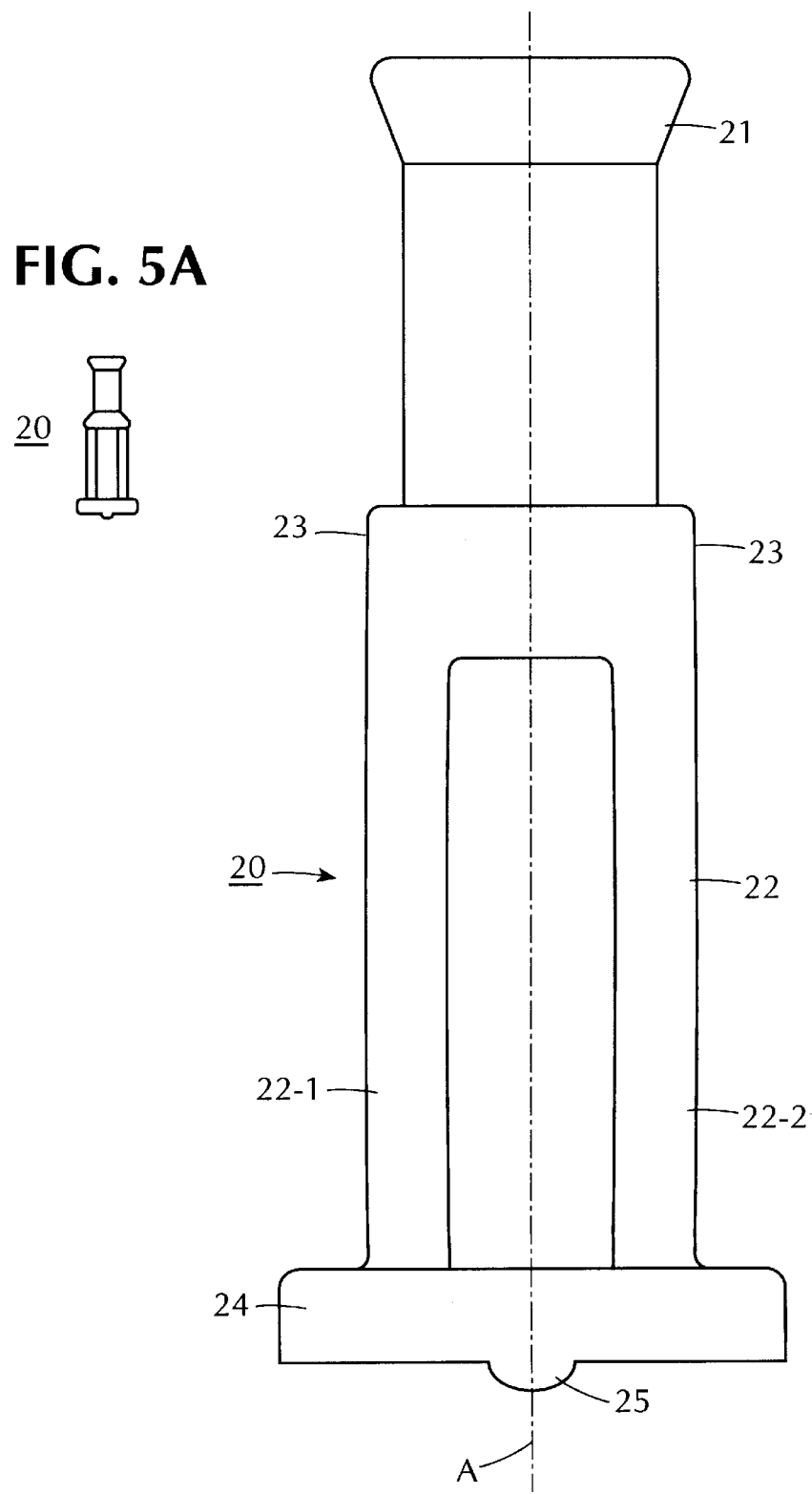

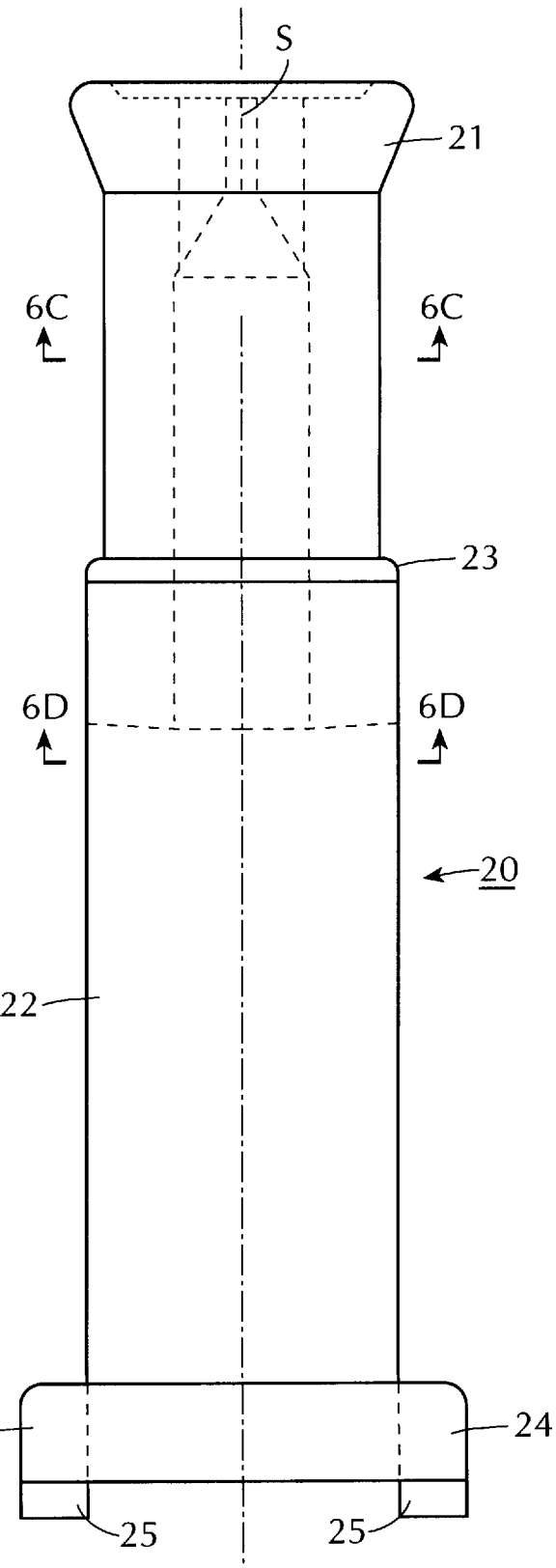
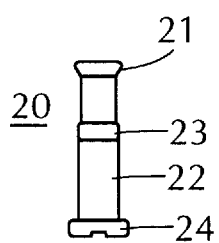
FIG. 6A
FIG. 6B

CONTROL OF FLUID FLOW

This application is a continuation of Ser. No. 08/290,136, filed Aug. 15, 1994, U.S. Pat. No. 5,699,821, which is a continuation-in-part of Ser. No. 08/135,673, filed Oct. 13, 1993, U.S. Pat. No. 5,509,433.

BACKGROUND OF THE INVENTION

The invention relates to flow control and more particularly, to the control of fluid flow with respect to the infusion and aspiration of fluids in venous and arterial systems.

A common container for medical fluids is a plastic pouch which contains saline, i.e. a salt solution used in investigation of biological and physiological processes. The contents of such a container are carried by a conduit, typically plastic tubing, through a "check" valve that is used to prevent backflow.

In addition, other check valves can be used with the conduit to provide for the infusion and/or aspiration of other substances, such as medicaments, body fluids, and anesthetics. Infusion is commonly used to introduce saline or other medical fluids into veins, while aspiration is commonly used to draw fluids from body cavities.

The ordinary check valve used with conduits from medicinal containers functions by the deflection of an elastomeric element towards and away from a valve seat. The deflection is towards the valve seat in order to prevent flow, and away from the seat to permit flow.

In some cases the control of fluid flow is with respect to a multiplicity of channels that have varying degrees of convergence with one another. A typical multichannel arrangement makes use of connectors which permit the intercoupling of flow channels. For example, when two channels are to be joined to permit a common output, the connector can take the form of a fitting that resembles a "Y". When one of the channels terminates in an infusion site, the prior practice has been to access the site by needles, which are undesirable.

Because of the desirability of achieving needleless injection and infusion of fluids, one effort has resulted in Rogers et al. U.S. Pat. No. 5,006,114 of Apr. 9, 1991, in which a valve assembly has a Luer lock on an inlet, and movable piston seals the inlet.

When a syringe is attached to the Rogers inlet the piston is displaced to unseal a fluid channel which connects the end of the syringe to an outlet, and then to a device connected to a patient. When the syringe is removed from the inlet the piston is moved to its original closed position by an internal spring of the valve. This device suffers from the disadvantage that the requirement of a spring for acting against the piston results in a force against the inserted Luer tip that increases as the piston is displaced.

In addition, the Rogers medical valve assembly provides an outlet channel that is displaced at an angle in relation to the inlet. As a consequence of this angular displacement, it is difficult to manufacture the device since there is a tendency for flash to accumulate at the entrance of the outlet channel in the vicinity of the piston. In addition, the angular configuration of the Rogers valve does not lend itself to manifold application.

Moreover, the Rogers design is intended for a Luer fitting which does not have a taper so that when the conventional tapered Luer fitting is employed, it can become jammed in the straight line walls of the inlet.

An attempt to overcome the disadvantages of Rogers is disclosed in Raines, U.S. Pat. No. 5,147,333, which issued Sep. 15, 1992. In the Raines patent there is accommodation for a tapered Luer fitting, but there is the continued disadvantage of the necessity for using a spring to urge a piston or spool forwardly during closure of the valve and rearwardly when the valve is being opened. As a result, the disadvantageous increase in spring force with displacement continues to be present.

Furthermore, the Raines "backcheck" valve requires a pair of vertically offset ports that extend laterally from a tubular body and the spool or piston is disposed between the ports. In addition, like the predecessor Rogers valve, the piston or spool in Raines requires at least one projection from the end of the piston contacted by a Luer tip in order to permit the flow of fluid from the Luer tip through the valve.

In addition, the Raines valve is subject to difficulties in manufacture because of flash since the various outlet ports are angularly, i.e., perpendicularly, oriented in relation to their inlets.

Other arrangements are disclosed in Newgard, U.S. Pat. No. 5,064,416; Sivert, U.S. Pat. No. 4,915,687 and Jackson, U.S. Pat. No. 4,429,856. These arrangements are complex, are difficult to manufacture and have numerous disadvantages.

Another objection to existing arrangements is that their activators are not interchangeable. Thus, injection sites that require needle injection cannot be used without needles; conversely injection sites that are externally actuated by inserting a member that opens a diaphragm cannot be used with needles. In addition, the non-needle injection sites present problems of sterility. In order to have external access to the control diaphragm, it is necessary to have an open channel that can become contaminated. Even when a temporary seal is provided for the open channel, removal of the seal prior to the injection allows inadvertent contamination. This is by contrast with an injection site having a needle-puncturable surface. The latter can be wiped clean with a sterilizing agent before injection is to take place.

Accordingly, it is an object of the invention to achieve needleless injection, infusion and aspiration without the need for spring-loaded members, such as pistons or spools where the counterforce exerted by the spring increases as the piston is displaced. A related object of the invention is to overcome the disadvantages characterizing the needleless injection valves of Rogers, U.S. Pat. No. 5,006,114 and Raines, U.S. Pat. No. 5,147,333.

A further object of the invention is to overcome the need for angular orientation of an outlet in relation to an inlet in order to avoid manufacturing difficulties such as the creation of flash which can clog or reduce the volume of fluid flow from an inlet to an outlet.

Yet another object of the invention is to permit the non-use of projections on a closure for an inlet, whereby a Luer fitting can open an inlet channel without the need for engaging one or more projections on a closure.

A further object of the invention is to enhance the control that can be achieved over fluid flow. A related object is to enhance flow control where fluid infusion or combination is to take place.

An important object of the invention is to eliminate the need for needle usage at injection sites, while permitting needle usage if that is desired. A related object is to maintain sterility at injection sites that are operated without needles, while simultaneously permitting such sites to be used with needles if necessary.

An additional object of the invention is to improve the performance of valves for infusion, injection, aspiration and control of fluid flow.

SUMMARY OF THE INVENTION

In accordance with the present invention, a flow control device is disclosed comprising an inlet for the flow of fluid, an outlet, and a conduit connecting the inlet to the outlet to enable fluid flow from the inlet to the outlet. The device includes a slidable movable plug having a compressible head with a first position in sealing engagement with the inlet and a second position out of sealing engagement with the inlet. A slot is provided through the flexible head for permitting fluid flow through the head when the head is in the second position. The flexible body comprises elongated legs which are flexed when the head is in the second position, for providing a return force for returning the head to its first position.

In accordance with another embodiment of the invention, a flow control device is disclosed having a normally open slotted and compressible head with a first position in sealing engagement with an inlet of the device, wherein the slot is closed by the inlet. The head has a second position within a conduit connecting the inlet to an outlet, wherein the head is out of sealing engagement with the inlet and the slot is opened. A flexible body depends from the head. The head is movably disposed between the first and second positions to permit flow from the inlet through the conduit when the head is moved from the first position to the second position. The flexible body comprises outwardly tapered and slotted outer walls forming legs which provide a force on the head when the flexible body is moved from the first position to the second position for returning the head to the first position from the second position.

A tapered bore is preferably provided within the conduit of the flow control device, extending from the inlet of the device. The normally open slotted and compressible head is movably disposed between a position in sealing engagement with the inlet and a position within the tapered bore. When the head is in the position sealing the inlet, the inlet closes the slot from a completely open to a completely closed condition.

In an alternative embodiment of the invention, a spring is coupled to the normally open slotted and compressible head, biasing the head towards the inlet. The head is movable by a force from an equilibrium position sealing the inlet, wherein the slot is closed, to a position opening the inlet, wherein the slot is opened, by an external force. Removal of the force causes the spring to return the head to its equilibrium position in sealing engagement with the inlet.

In accordance with another embodiment of the invention, the normally open slotted and compressible head has an outer peripheral surface with longitudinally extending grooves. The slot of the head is in the form of a multi-sided geometric figure with opened segments when the head is in the non-sealing position.

A method of fabricating a flow control device in accordance with the present invention is also disclosed, including (a) molding an inlet member having an axis of flow, an inlet, a coaxial seat beyond the inlet, and an expansion chamber beyond the coaxial seat; (b) molding a rectangular outlet member which complements the inlet member and has a rectangular coaxial support; (c) inserting an expandable control member into the inlet member, wherein the control member has before insertion, a normally open slot and the inlet closes the slot; and (e) joining the outlet member to the inlet member with the expandable control member therein and the slot closed.

DESCRIPTION OF THE DRAWINGS

FIG. 3A is a scale view of the other side of the flow-control valve of FIG. 1A in accordance with the invention;

FIG. 3B is an enlarged sectional view of the flow-control valve of FIG. 3A in its closed valve position;

FIG. 5A is a scale view of one side of a flow-control plug for the valve of FIG. 1A;

FIG. 5B is an enlarged view of the flow-control plug of FIG. 5A in its "pre-installation" condition;

FIG. 6A is a scale view of the other side of the flow-control plug for the valve of FIG. 1A;

FIG. 6B is an enlarged view of the flow-control plug of FIG. 6A in its "pre-installation" condition;

FIGS. 10A through 10E are end views of alternative tips for plugs in accordance with the invention;

DETAILED DESCRIPTION

Figure 1A:
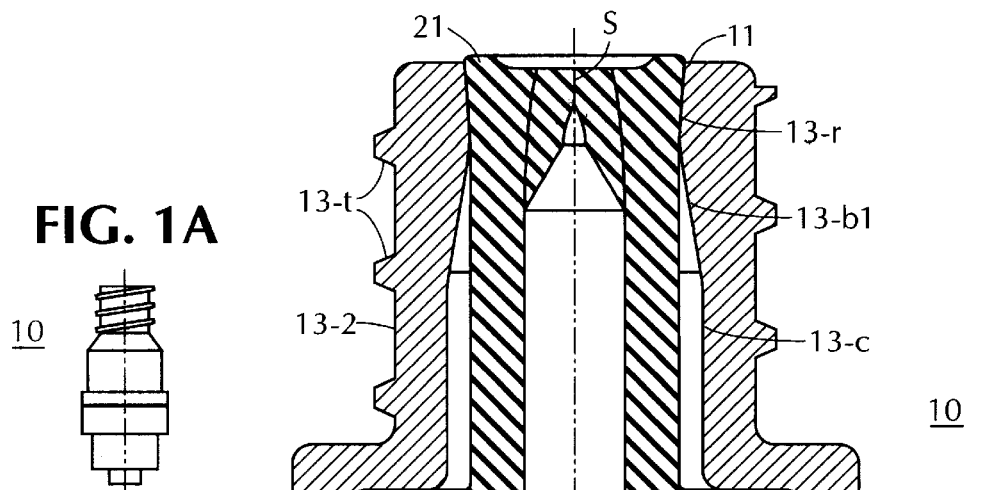
FIG. 1A is a scale view of one side of a flow-control valve in accordance with the invention.

FIGS. 1A and 3A are scale views of different sides of a flow-control valve 10 in accordance with the invention. The valve 10 is rectangular in cross-section having the specific configuration described in detail below, with FIG. 1A showing the longer side and FIG. 3A showing the shorter side.

Figure 1B:
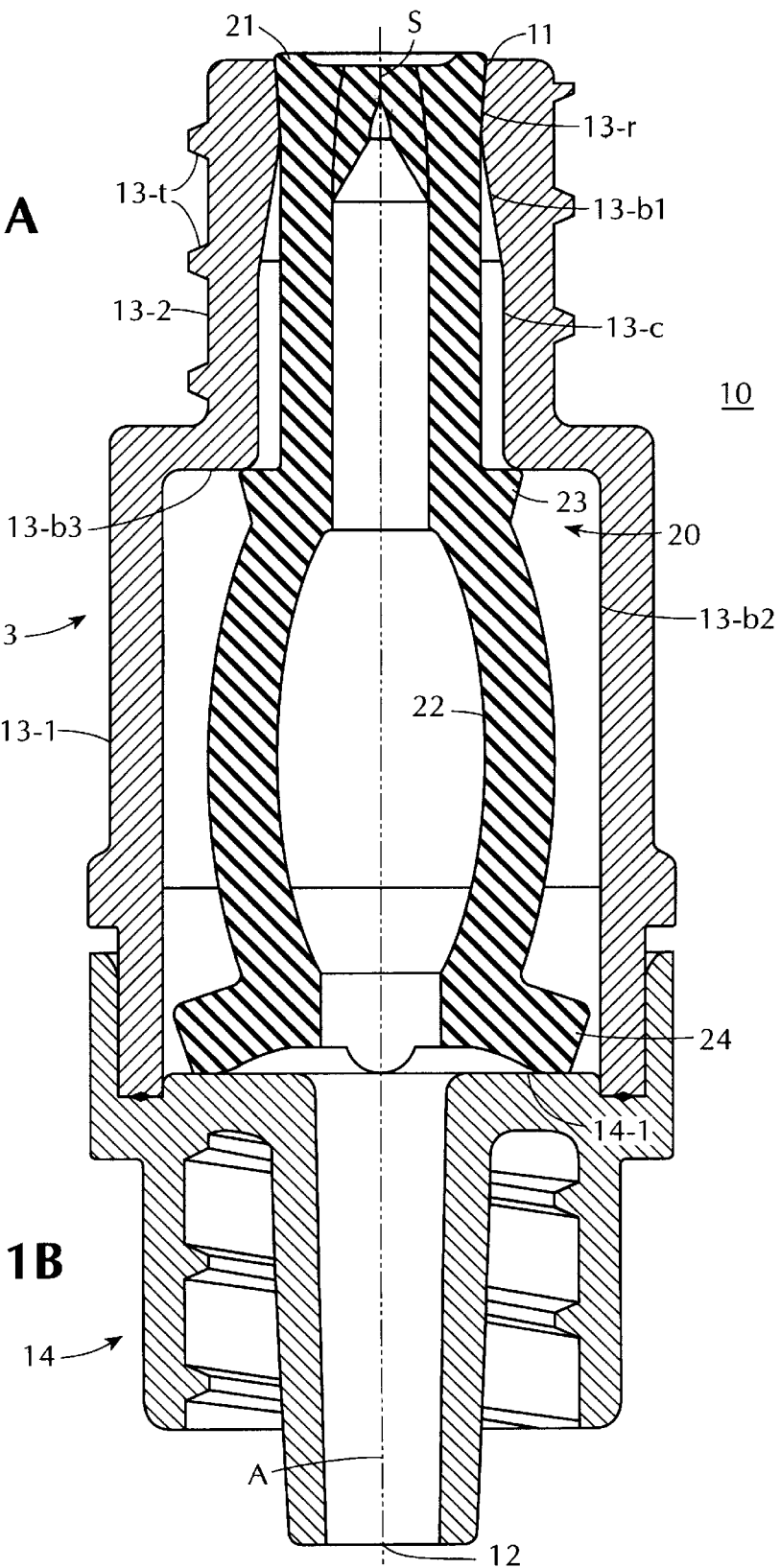
FIG. 1B is an enlarged sectional view of the flow-control valve of FIG. 1A in its closed valve position.

In FIG. 1B, which is an enlarged sectional view, the flow-control valve of FIG. 1A is shown in its "pre-loaded" condition with its inlet 11 through the slot S sealed by the head 21 of a depressible plug 20. As indicated in FIG. 1B, the head 21 of the plug 20 has a closed slot S. In addition, the valve 10 has an outlet 12 connected to the inlet 11 and disposed to serve as a conduit for the throughflow of fluid that is applied at the inlet 11.

Figure 2A:
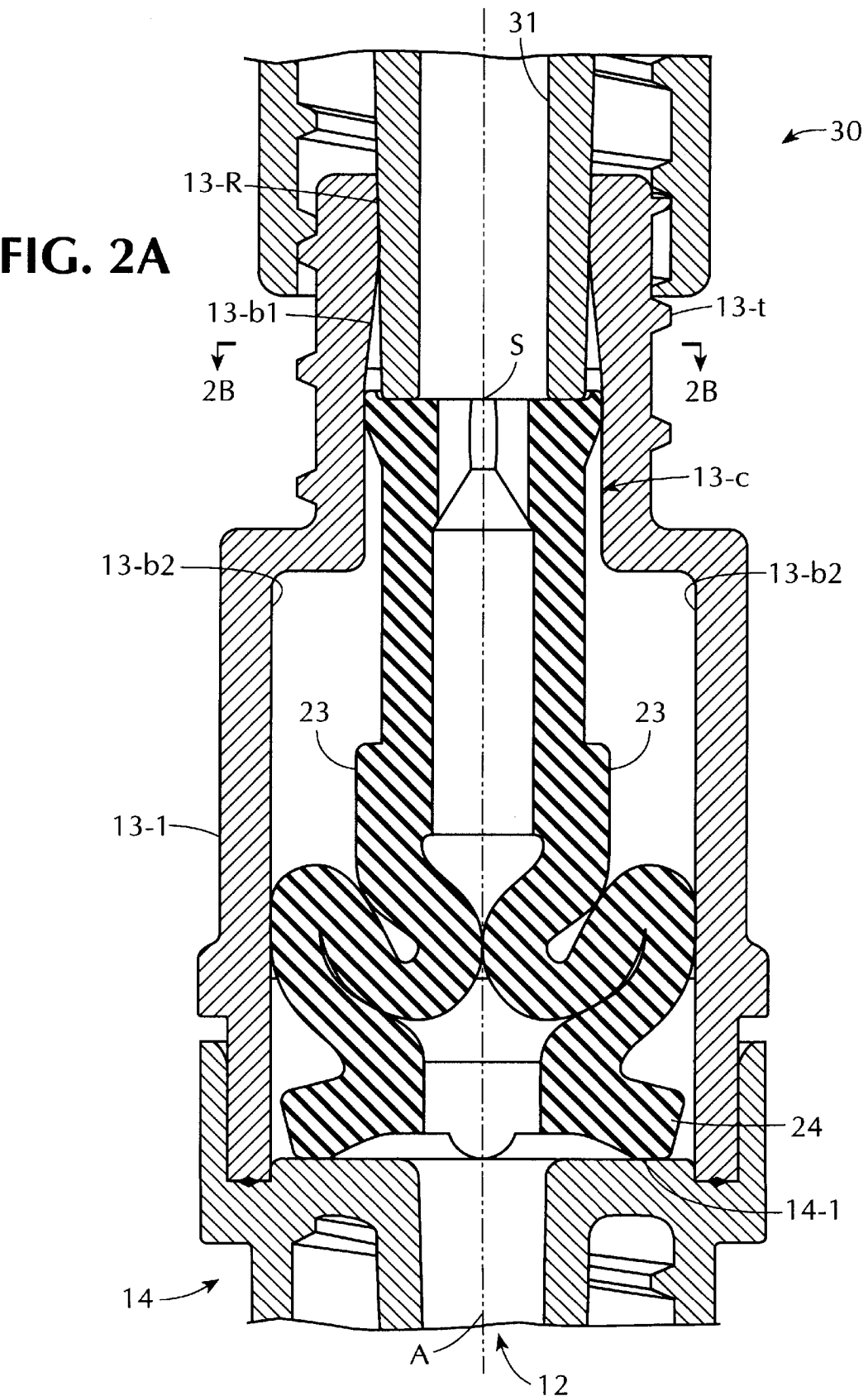
FIG. 2A is an enlarged sectional view of the flow-control valve of FIG. 1A in its "operational flow" position with an external pressure member.

The depressible plug or movable member 20 (as shown further in FIGS. 5A through 6E) has a flexible head 21 which seals the inlet 11 and extends to a flexible body 22 for controlling flow by the outward flexing of the body 22 when the head 21 is depressed as indicated in FIG. 2A.

In effect, the plug 20 forms a bell-shaped member with a hollow head 21 and a slotted body 22. The base of the body 22 terminates in a circumferential rectangular base 24. The rectangularity avoids twisting during compression.

In the flow control device 10, the movable plug 20, together with the head 21 and the flexible body 22, extends between the inlet 11 and the outlet 12. The flexible body 22 is expandable laterally with respect to the vertical axis A of the outlet channel 12 in order to create spring pressure during opening and closing of slot s. Consequently, the upper housing 13 has an enlarged expansion chamber 13-1. In addition, the housing 13 has a neck 13-2 with exterior Luer threads 13-*t* and an inwardly tapered bore 13-*b*1 beyond an interior cylindrical rim 13-*r*. Extending from the inwardly tapered bore 13-*b*1 is a cylindrical bore 13-*c* which, in turn, extends to a rectangular wall 13-*b*2. The rectangular wall 13-*b*2 extends to the expansion chamber 13-1.

A shoulder 23 of the plug 20 engages the horizontal wall 13-*b*3 proximate the bore 13-*c* of the expansion chamber 13-1. The head 21 seals the inlet 11 by being compressed against the inwardly tapered bore 13-*b*1 and the cylindrical rim 13-5, as described below. The head 21 remains in sealing contact with the tapered bore 13-*b*1 of the neck 13-2, and then with the bore 13-*c*, as the plug is depressed.

Figure 2B:
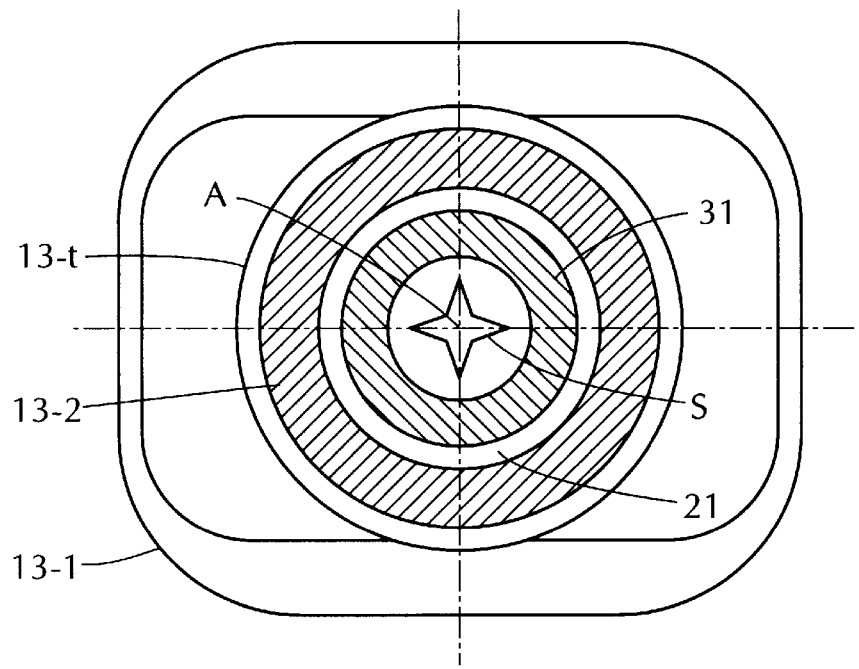
FIG. 2B is a sectional view of the flow-control valve of FIG. 2A taken along the lines 2B—2B.
Figure 4A:
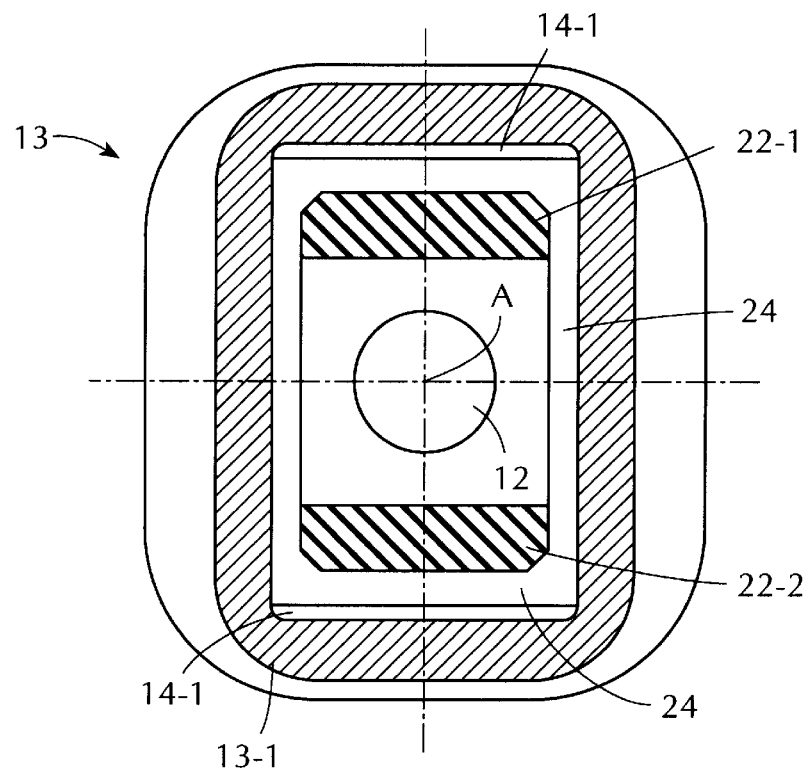
FIG. 4A is a sectional view of the flow-control valve of FIG. 3A taken along the lines 4A—4A.

However, when the bore 13-*c* at the end of the tapered bore 13-*b*1 is reached, the slot S opens, as shown in FIGS. 2A and 2B. Within the expansion chamber 13-1, the two legs of the body 22 can be spaced from the rectangular walls as shown in FIG. 4A.

For the embodiment of FIGS. 1B, 2A and 3B, the head 21 of the plug 20 has an upper slot 21-*s* so that when a Luer tip, such as the tip 31 of FIG. 2A is threaded on the neck 13-2 it seals circumferentially on top of plug 20 and there is no impediment to flow from the interior of the tip 31. This embodiment is particularly useful for relative low pressure infusion of fluids, e.g. by gravity flow from a saline bag (not shown). It is to be noted that because of the slot 21-*s*, pressure against the outer surface of the head 21 does not cause a collapse of material which could block the tip 31.

The Luer tip 31 thus permits activation of the control plug by a member external to the flow control device 10 since the plug 20 is seated in the inlet 11 and can be depressed from its compressed seal position to the bore 13-*c*. In effect the control is by a bell-shaped member with its upper portion sealing the inlet, and walls straddling the outlet. The walls are extended legs 22-1 and 22-2 which are bowed under pressure in the axial direction of the outlet channel 12. The slotted walls 22-1 and 22-2 are flexed or buckled under pressure. They extend from the head 21 sealing the inlet 11 to a base 14-1 of a lower body 14 encircling the outlet channel 12.

Figure 2C:
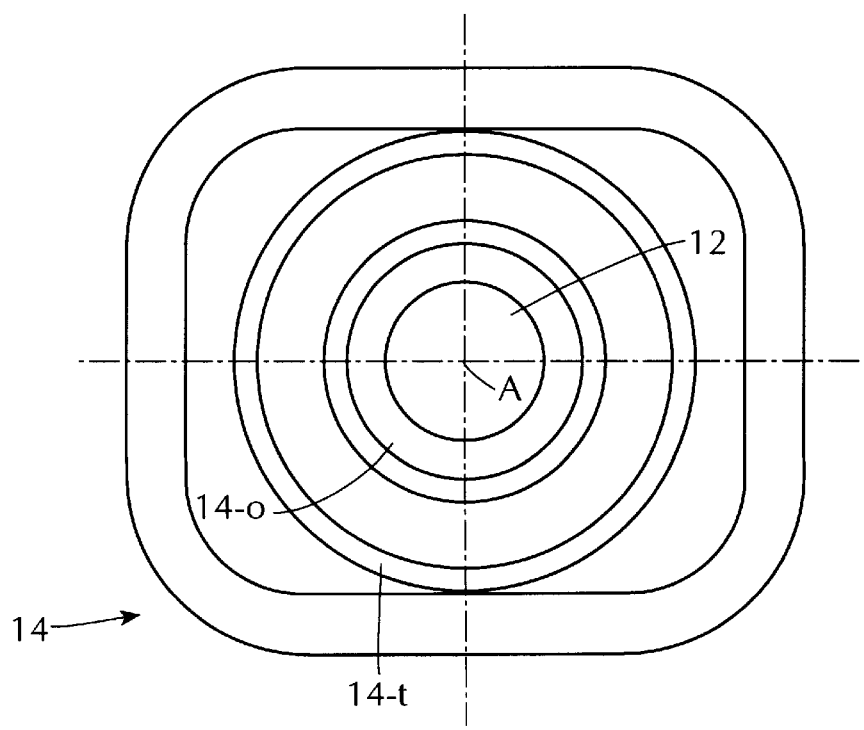
FIG. 2C is a bottom view of the flow-control valve of FIG. 2A.
Figure 4B:
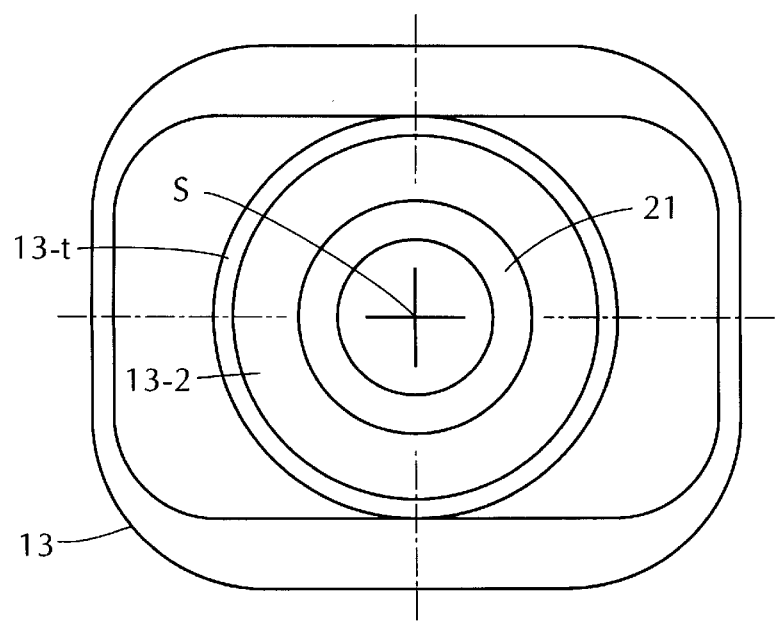
FIG. 4B is a top view of the flow-control valve of FIG. 3A.

FIG. 2B is a sectional view of the flow-control valve of FIG. 2A taken along the lines 2B—2B, while FIG. 2C is a bottom view of the flow-control valve of FIG. 2A. FIG. 3B is an enlarged sectional view of the flow-control valve of FIG. 3A in its closed condition, while FIG. 4A is a sectional view of the flow-control valve of FIG. 3A taken along the lines 4A—4A, and FIG. 4B is a top view of the flow-control valve of FIG. 3A.

The component elements 13 and 14 are locked together by snap action, but can be joined, for example, by ultrasonic welding. The valves of the invention promote sterility by providing ease of accessibility. Prior art valves with recessed stoppers allow antimicrobial agents to accumulate in puddles on the tops of stoppers. Particulate matter may also collect on recessed tops.

Figure 5C:
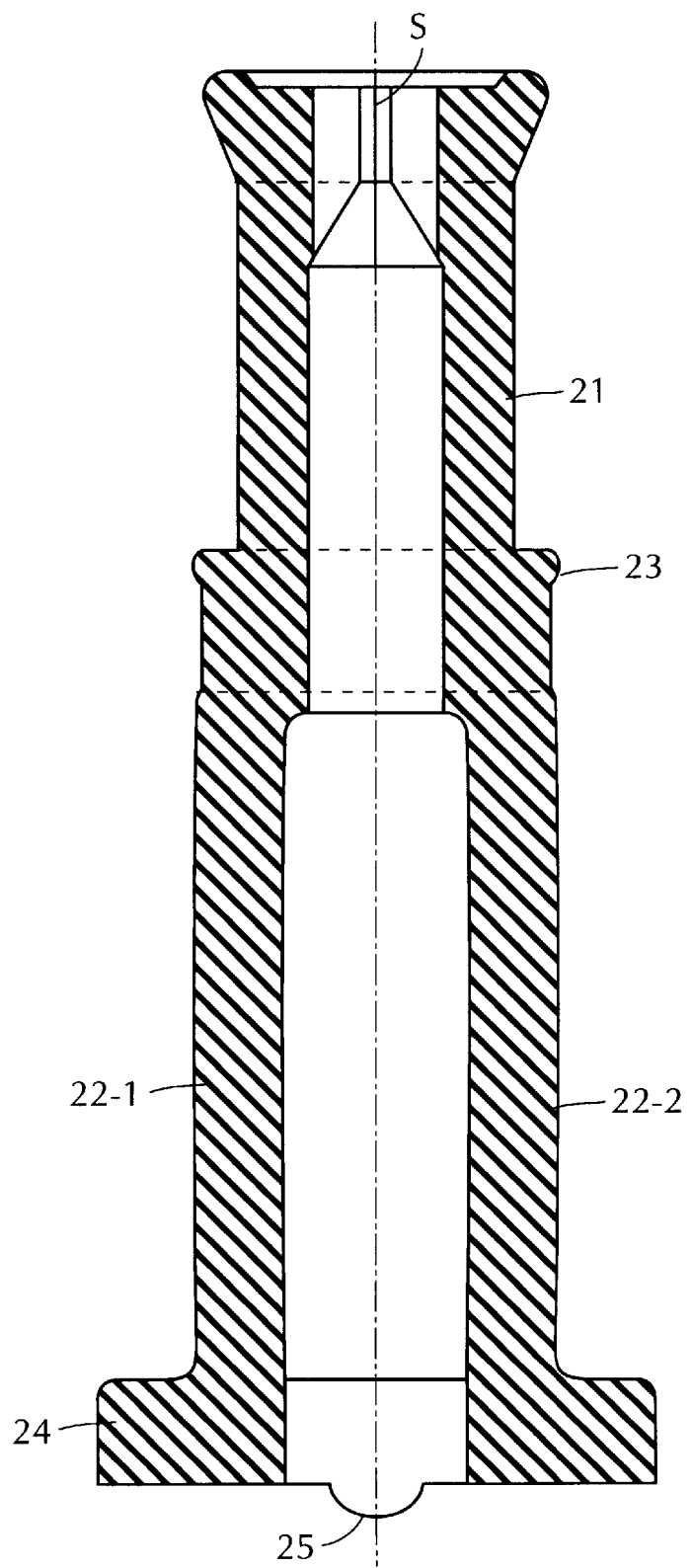
FIG. 5C is an enlarged sectional view of the flow-control plug of FIG. 5B in its "pre-installation" condition.
Figure 5D:
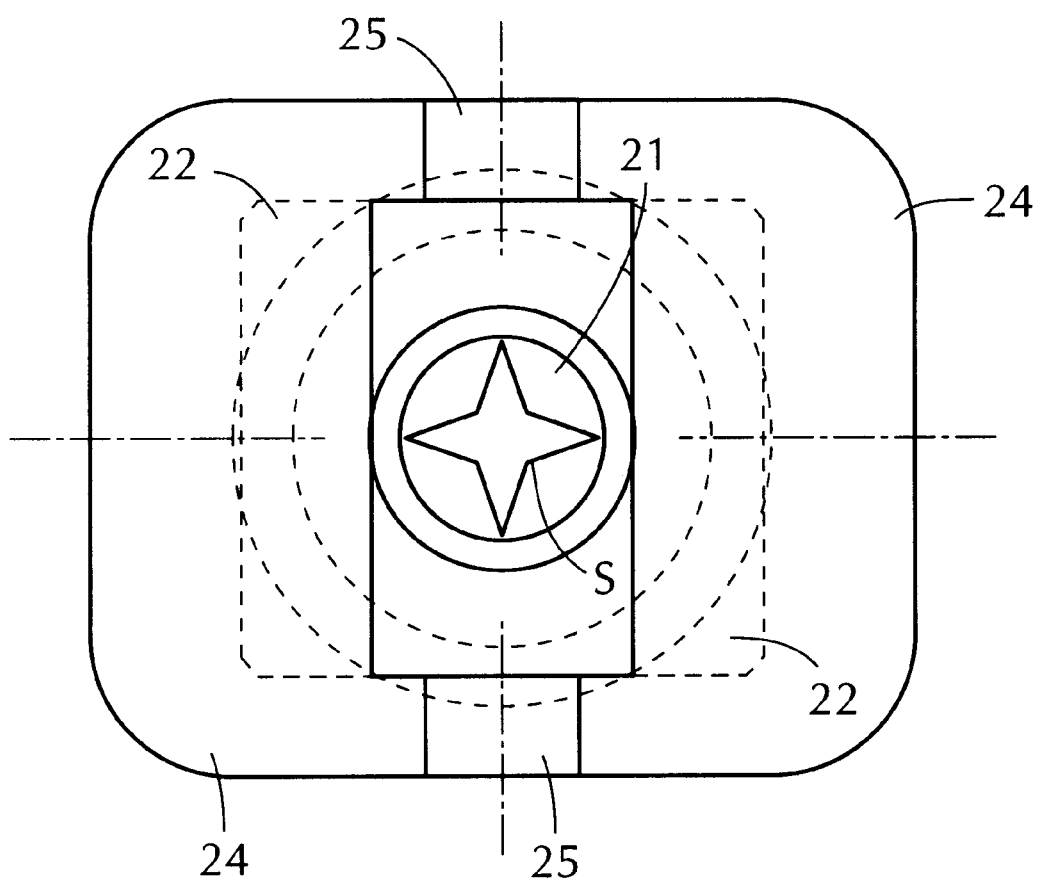
FIG. 5D is a bottom view of the flow-control plug of FIGS. 5B and 5C.

FIG. 5A is a scale view of one side of a flow-control plug 20 for the valve 10 of FIG. 1A, and FIG. 5B is an enlarged view of the flow-control plug of FIG. 5A in its "pre-installation" condition, while FIG. 5C is an enlarged sectional view of the flow control plug of FIG. 5B in its "pre-installation" condition with a star-shaped slot S. FIG. 5D is a bottom view of the open, star-shaped slot S in the flow-control plugs of FIGS. 5B and 5C.

Figure 6C:
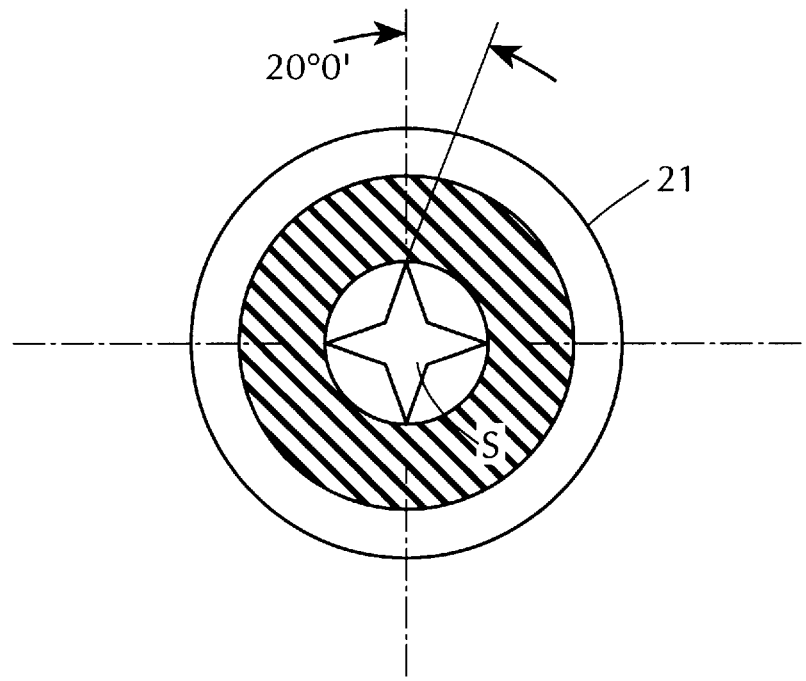
FIG. 6C is a sectional view of the flow-control plug of FIG. 6B in its "pre-installation" condition taken along the Fines 6C—6C.
Figure 6D:
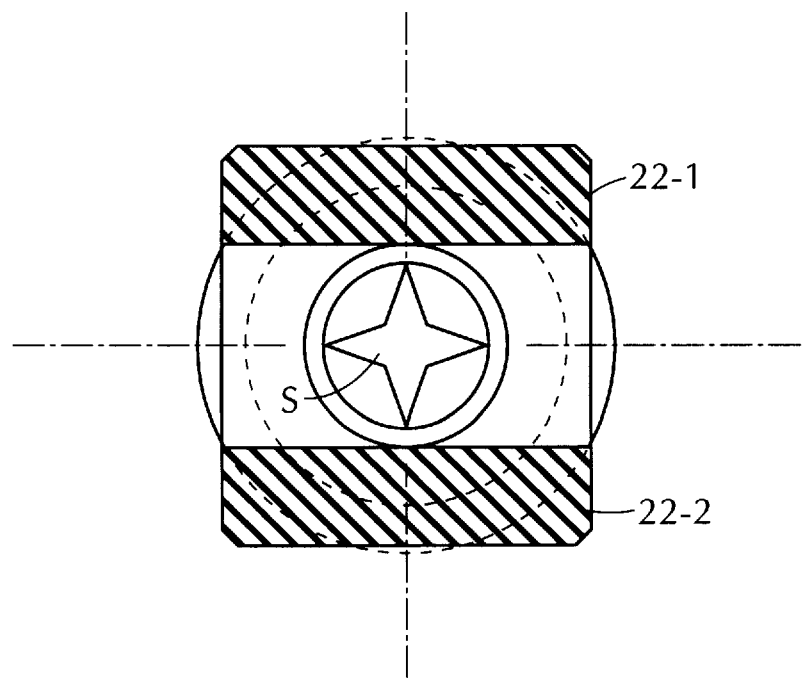
FIG. 6D is a sectional view of the flow-control plug of FIG. 6B taken along the lines 6D—6D.
Figure 6E:
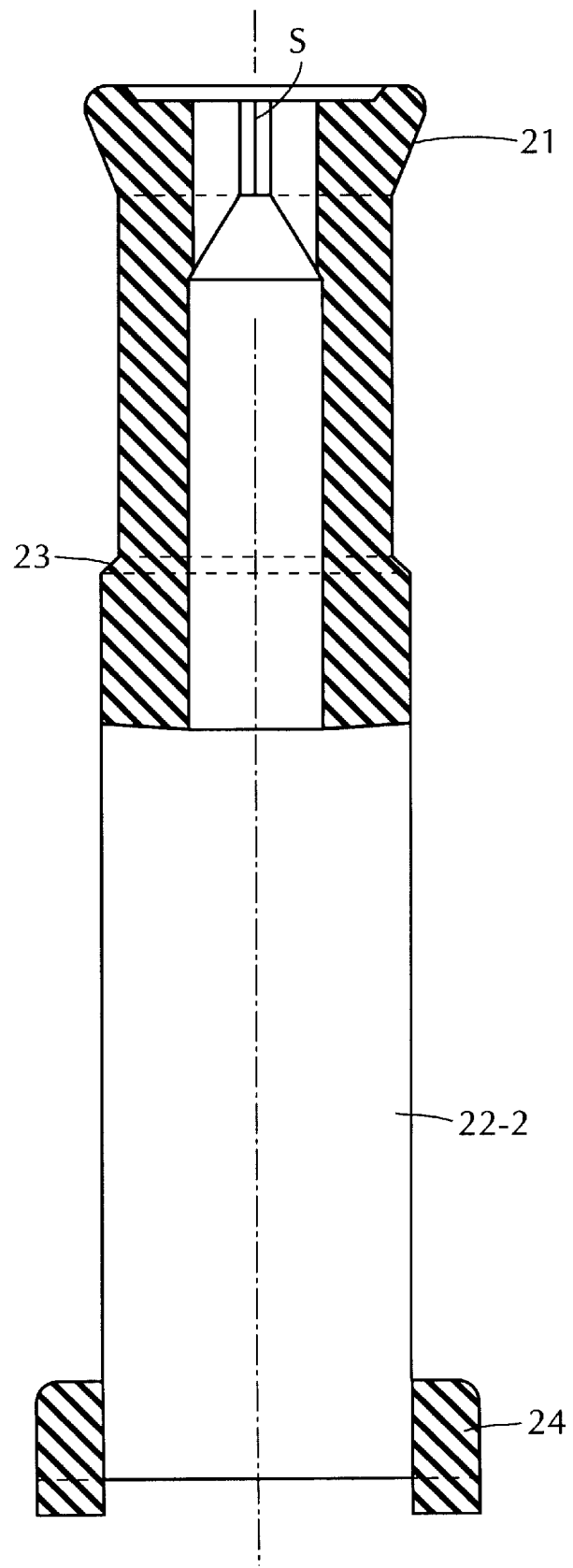
FIG. 6E is a sectional view of the flow-control plug of FIG. 6B.

FIG. 6A is a scale view of the other side of the flow-control plug for the valve of FIG. 1A, and FIG. 6B is an enlarged view of the flow-control plug of FIG. 6A showing the open star-shaped slot S in phantom in its "pre-installation" condition. FIG. 6C is a sectional view of the flow-control plug of FIG. 6B in its "pre-installation" condition taken along the lines 6C—6C, showing the open star-shaped slot S, and FIG. 6D is a sectional view of the flow-control plug of FIG. 6B taken along the lines 6D—6D, while FIG. 6E is a sectional view of the flow-control plug of FIG. 6B.

Figure 7A:
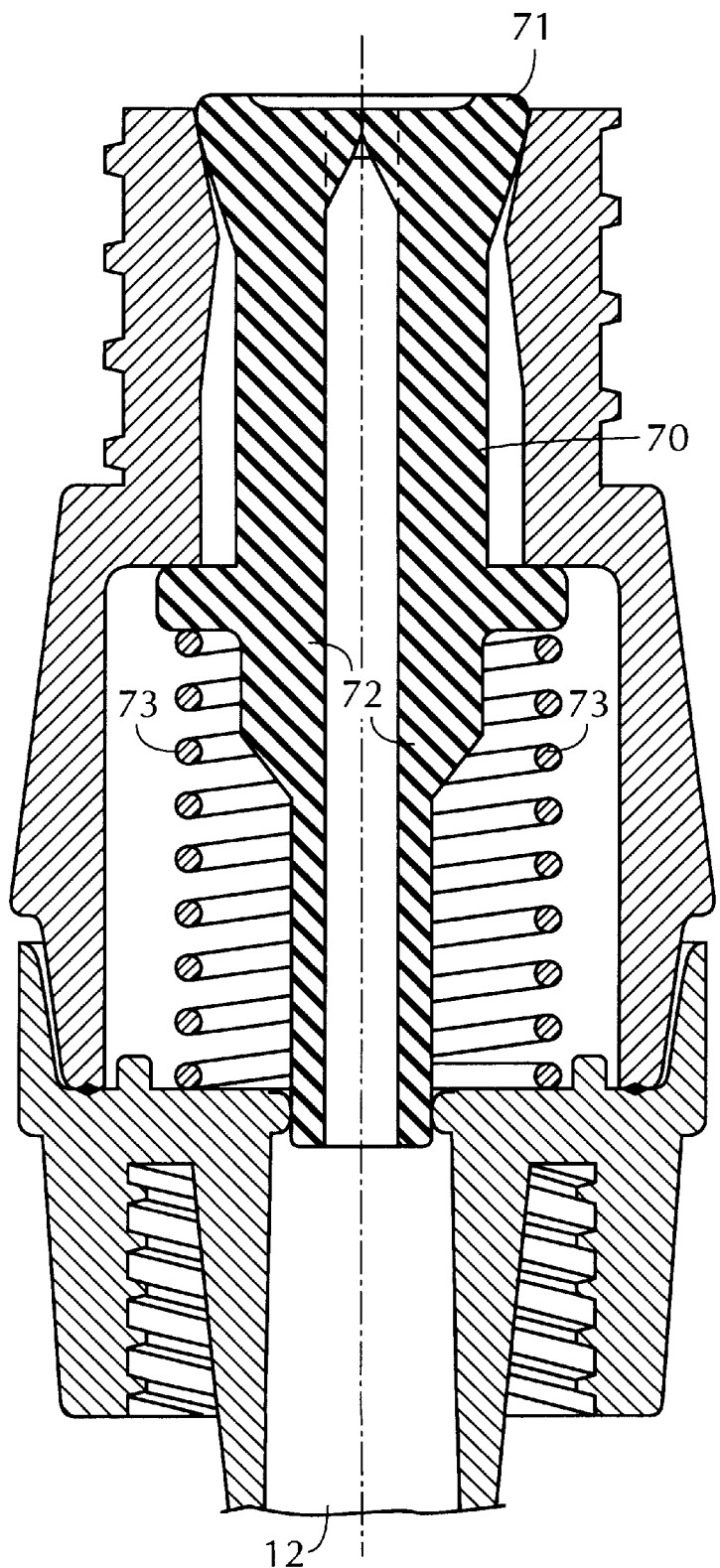
FIG. 7A is a cross-sectional view of an alternative flow-control valve in accordance with the invention.
Figure 7B:
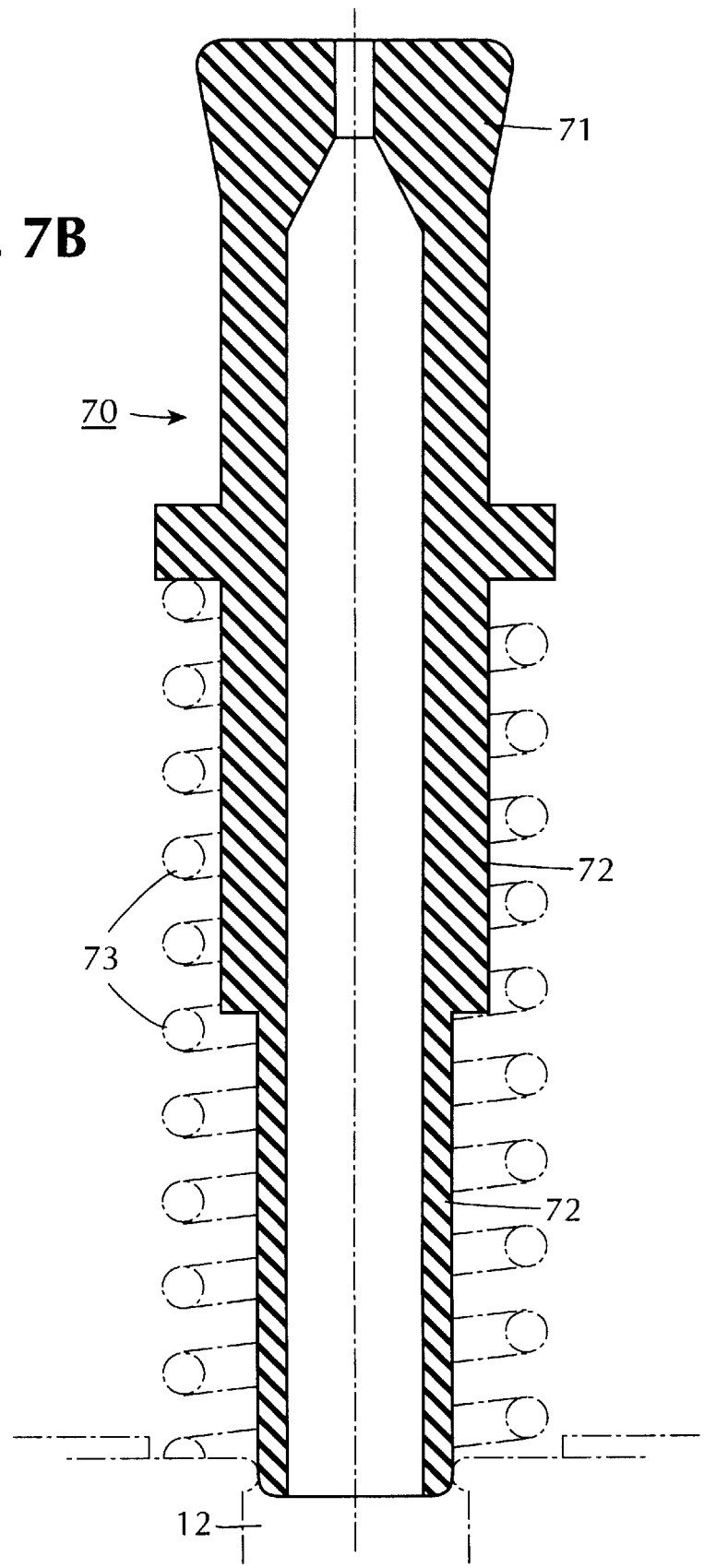
FIG. 7B is an enlargement showing details for the spring-loaded plug of FIG. 7A.
Figure 8A:
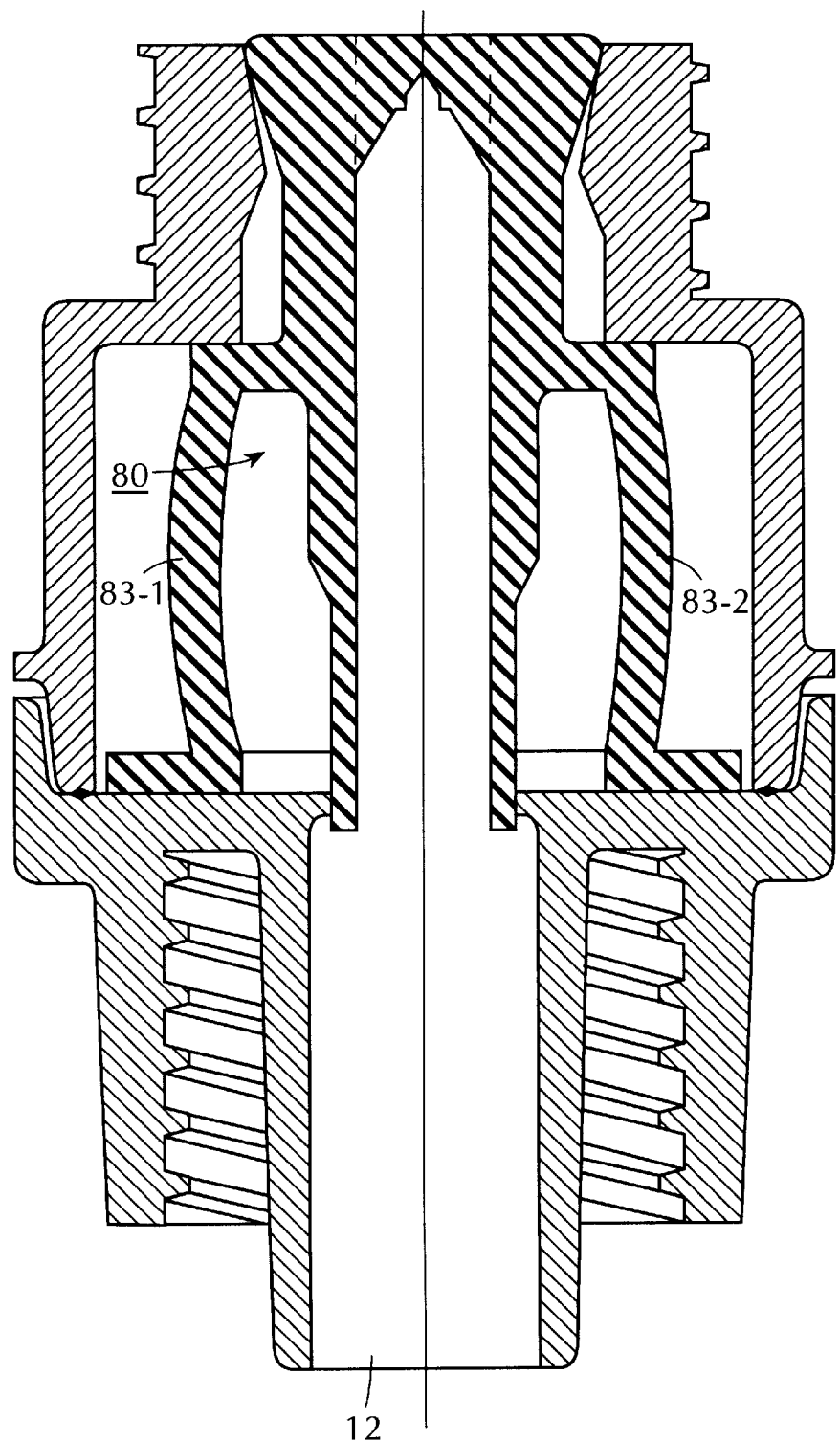
FIG. 8A is a cross-sectional view of an alternative to the flow-control valve of FIG. 7A in accordance with the invention.
Figure 8B:
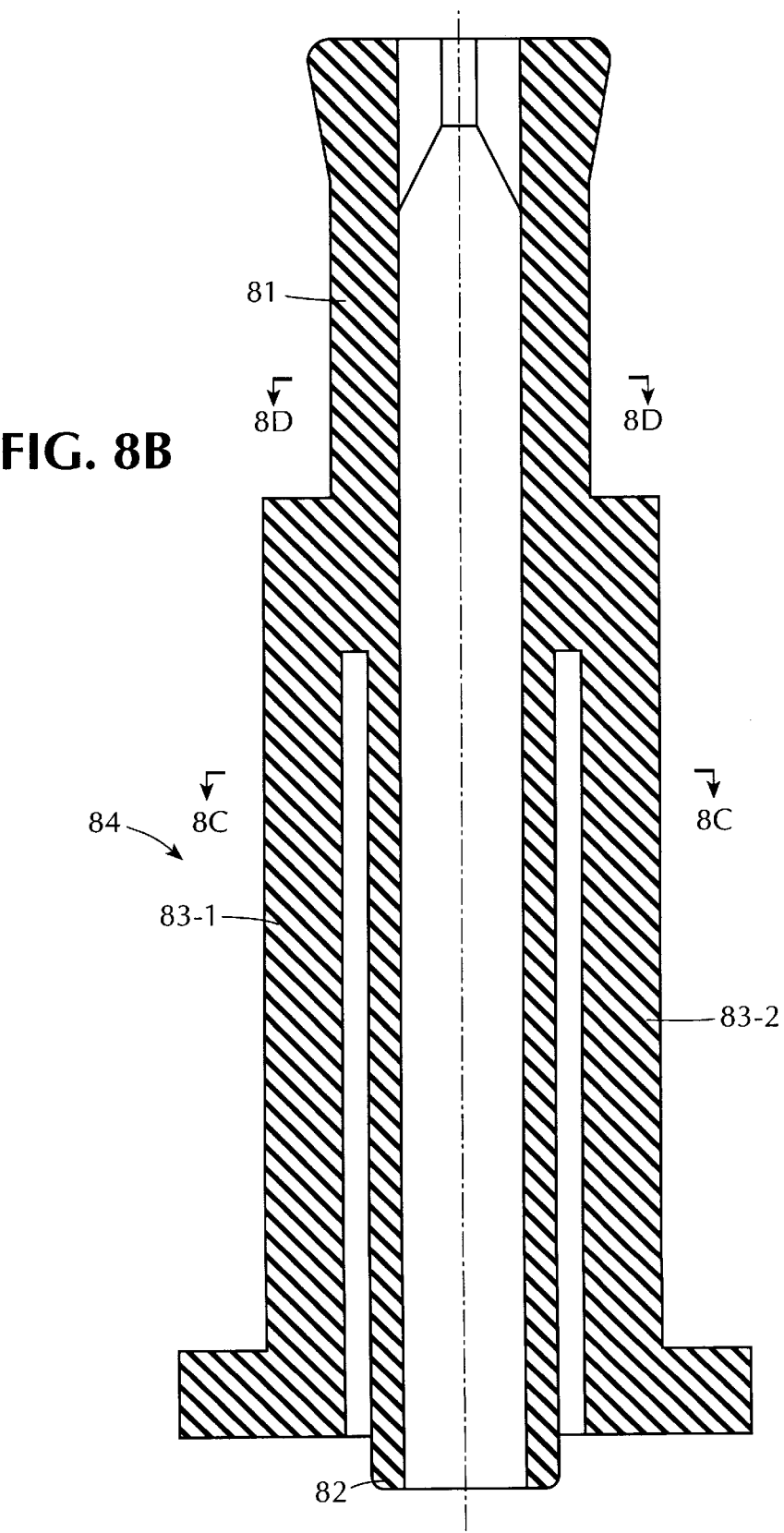
FIG. 8B is an enlargement showing alternative details for the plug of FIG. 8A.
Figure 8C:
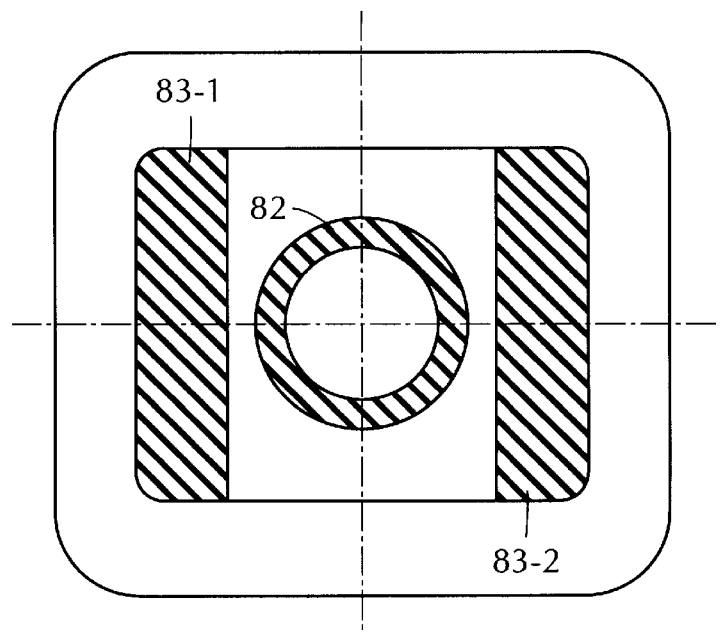
FIG. 8C is a cross-sectional view of the plug of FIG. 8B taken along the lines 8C—8C.
Figure 8D:
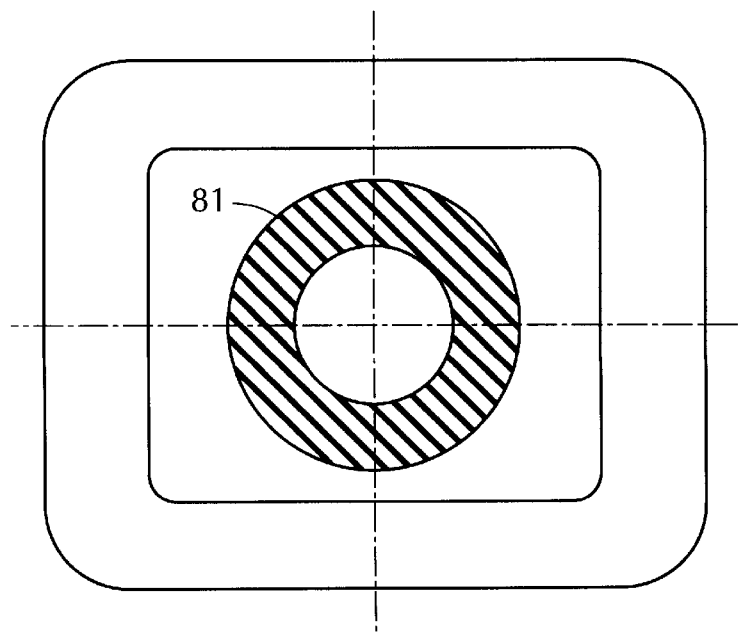
FIG. 8D is a cross-sectional view of the plug of FIG. 8B taken along the lines 8D—8D.

An alternative flow control plug 70 in accordance with the invention is shown in FIG. 7A. The plug 70 is used with the same general outer structure as the device 10 of FIG. 1A. However the plug 70 has a closed channel 72 which extends from a head 71 (like the head 11 of FIG. 1A) and is freely movable into the outlet 12 when the head is depressed. In order to restore the plug to its equilibrium condition when pressure to the head is removed, the plug 70 includes a spring 73, which is metallic in FIGS. 7A and 7B. A non-metallic, e.g. plastic spring, comprising resilient legs 83-1 and 83-2, is shown in FIG. 8A. FIG. 8B shows an alternative shaped plug with a head 81 and a spring portion 84, also comprising resilient legs 83-1 and 83-2. It will be appreciated that a metallic spring does not cause contamination in the embodiment of FIGS. 7A and 7B because the closed channel prevents fluid contact with the spring.

Figure 9A:
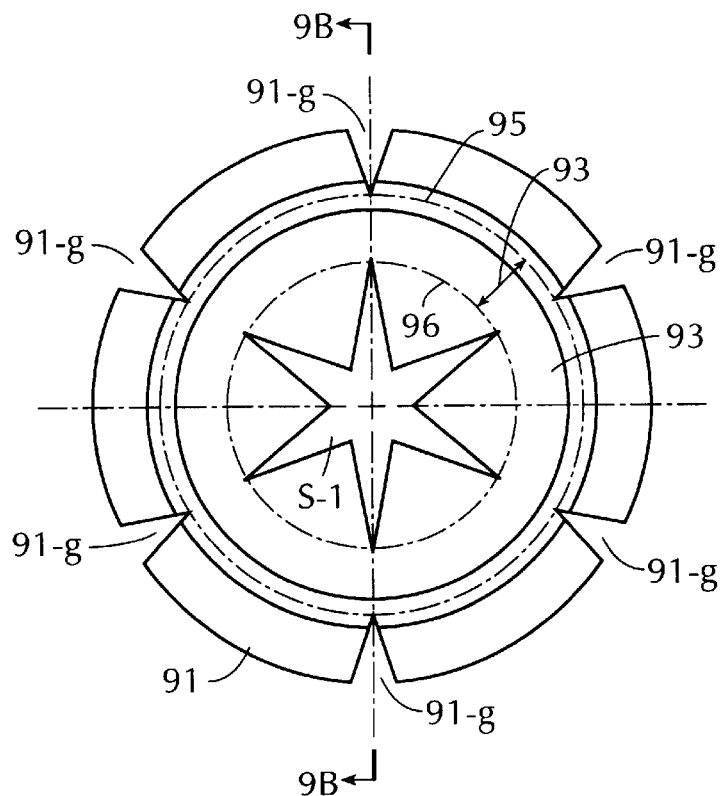
FIG. 9A is an enlarged end view of an alternative tip for the plugs of FIGS. 1A through 8D.
Figure 9B:
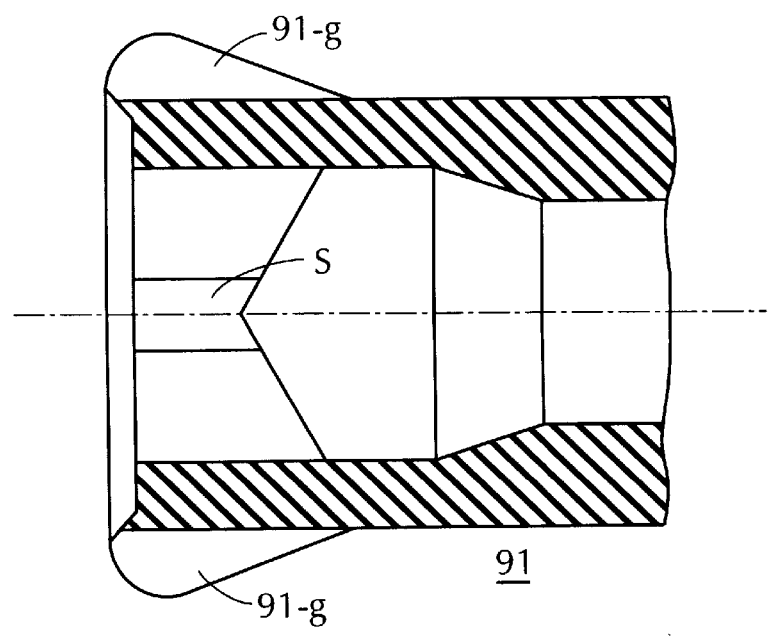
FIG. 9B is a partial cross-section of the tip of FIG. 9A taken along the lines 9B—9B.
Figure 10A:
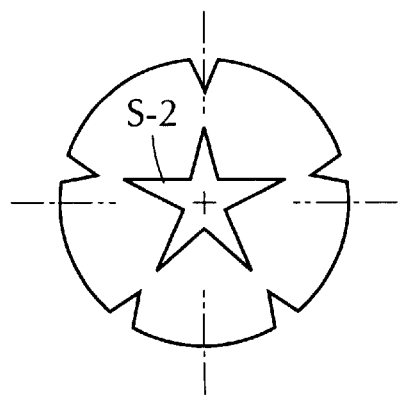
Figure 10B:
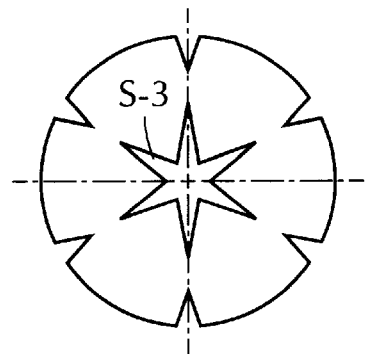
Figure 10C:
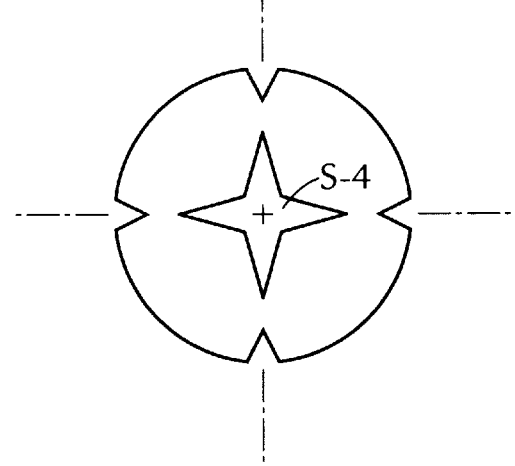
Figure 10C:
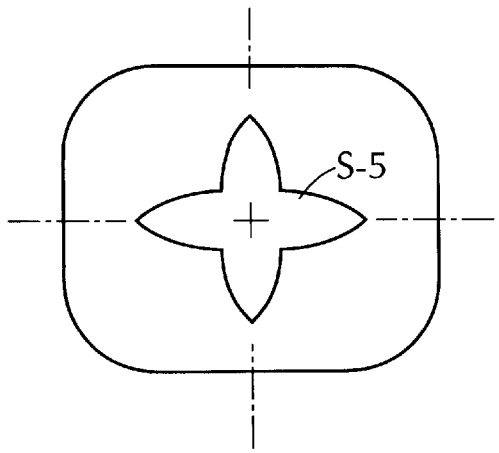
Figure 10E:
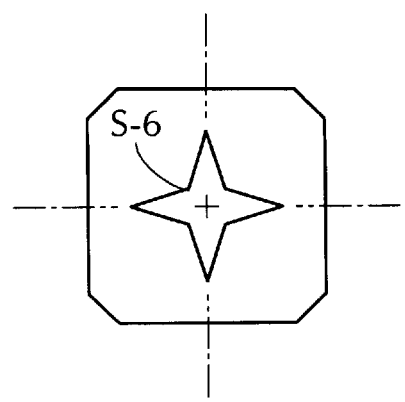

In order to facilitate the sealing of the head 11 it desirably takes the modified form 91 shown in FIGS. 9A and 9B with side grooves 91-*g*. In addition, the open, star-shaped slot S-1 of FIG. 9A is six-pointed, with segments to facilitate complete closure of the slot S-1 when the valve is sealed. Still other forms for the slot S are illustrated by the open slots S-2 through S6 of FIGS. 10A through 10E. In addition the heads of FIGS. 10B and 10E are square, as shown in FIG. 10E, or rectangular, as shown in FIG. 10D. The ring defined by the phantom lines 95, 96 indicates the region of contact between an externally activating male Luer and the top surface of the head 91.

Figure 11A:
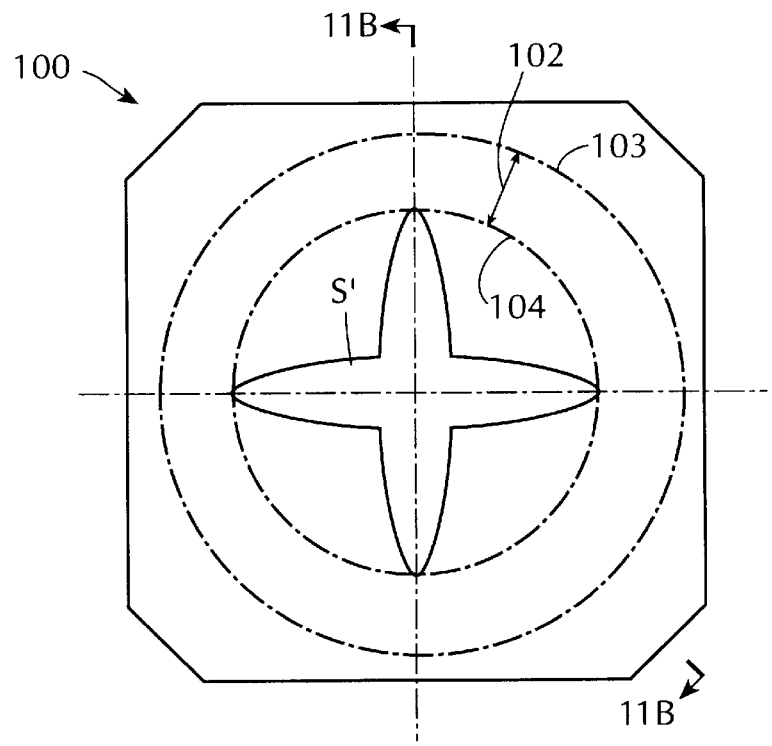
FIG. 11A is an enlarged end view of an alternative tip for the plugs of FIGS. 1A through 8D.
Figure 11B:
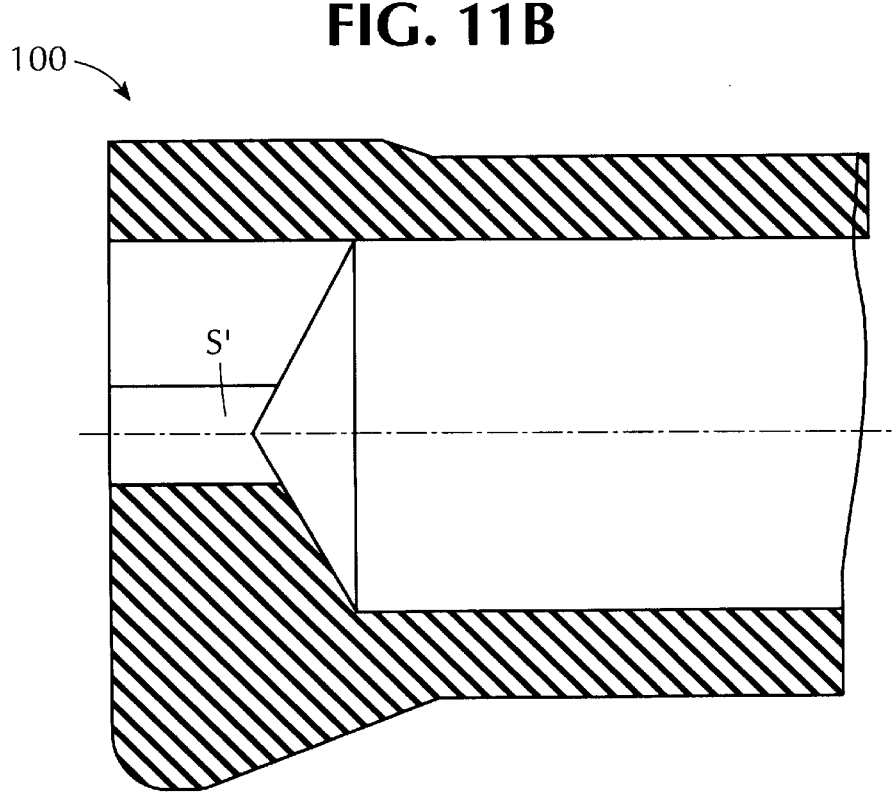
FIG. 11B is a partial cross-section of the tip of FIG. 11A taken along the lines 11B—11B.

A square plug similar to that of FIG. 10, except for having an open, star-shaped slot S' with arcuate sides, is shown in FIG. 11A. FIG. 11B is a partial cross-section of the square plug taken along the lines 11B—11B in FIG. 11A. This form of plug achieves the same kind of sealing effect that is achieved by use of the grooves 91-g in FIGS. 9A and 9B.

It will be understood that the foregoing embodiments are illustrative only and that modifications and adaptations of the invention may be made without departing from its spirit and scope as defined in the appended claims.

What is claimed:

1. A flow control device comprising:
    a valve body having an inlet and an outlet;
    the valve body defining in part a conduit for fluid flow through the valve body; and
    a slidable movable plug having a compressible head and a flexible body connected to the compressible head, the head having a first position in sealing engagement with the inlet and a second position out of sealing engagement with the inlet, the compressible head having a slot therethrough for permitting flow of fluid through the head and the conduit when the head is in the second position;
    the flexible body comprising elongated legs which are flexed when the head is in the second position, for providing a return force for returning the head to the first position.

2. The flow control device of claim 1, wherein the elongated legs are outwardly tapered.

3. The flow control device of claim 2, wherein the valve body further defines a first bore forming the inlet, a second bore extending from and being tapered inwardly towards the first bore, and a third bore with a straight wall, the third bore extending from the second bore towards the outlet the second position of the head being within the third bore, and a fourth bore extending from the third bore towards the outlet, the elongated legs being positioned within a region defined by the fourth bore, the slot of the head opening and the elongated legs flexing laterally with respect to the axis of the outlet within the fourth bore as the head is moved through the second bore, into the third bore, the slot completely opening when the head is in the second position within the third bore.

4. The flow control device of claim 3, wherein the valve body further comprises a well connected to the fourth bore, wherein a portion of the valve body defining the outlet extends from the well, the fourth bore and the well are rectangular in cross section as viewed along an axis passing through the inlet and the outlet, the flexible body has a substantially rectangular cross section as viewed along the axis and the flexible body has a first end connected to the head, a second end, and a rectangular base connected to the second end of the flexible body, sitting in the well.

5. The flow control device of claim 1, wherein the valve body defines a first bore forming the inlet, and a second bore extending from the inlet, the second bore being tapered inwardly towards the first bore, the slot of the head opening when the head is moved to the tapered bore.

6. The flow control device of claim 1, wherein the valve body comprises at least two interior opposing flat walls, each wall being parallel to a side of each of the elongated legs for preventing twisting of the elongated legs when the legs are flexed.

7. The flow control device of claim 1, wherein the valve body has an exterior having at least one flat surface.

8. The flow control device of claim 1, wherein the head is movable from the first position to the second position by a member external to the flow control device which does not penetrate the slot of the head, the head returning to the first position from the second position when the member is removed.

9. A flow control device comprising:
    an inlet;
    an outlet;
    a conduit connecting the inlet to the outlet enabling fluid flow from the inlet to the outlet;
    a normally open slotted and compressible head having a first position in sealing engagement with the inlet, wherein the slot is closed by the inlets and a second position wherein the head is out of sealing engagement with the inlet and the slot is opened;
    a flexible body depending from the head;
    the head being movably disposed between the first and second positions for permitting flow from the inlet through the conduit when the head is moved from the first position to the second position;
    the flexible body comprising outwardly tapered and slotted walls forming legs, the legs providing a force on the head when the flexible body is moved from the first position to the second position for returning the head to the first position from the second position.

10. The flow control device of claim 9, further comprising a valve body defining the inlet and the outlet, the valve body further defining a bore extending from and being inwardly tapered towards the inlet, wherein the second position is within the tapered bore.

11. The flow control device of claim 10, wherein the conduit is defined in part by the compressible head.

12. The flow control device of claim 11, wherein the conduit is further defined, at least in part, by the flexible body.

13. The flow control device of claim 11, wherein the conduit is further defined, at least in part, by the valve body.

14. A flow control device comprising:
    a valve body defining an inlet, an outlet and a tapered bore tapered inwardly toward the inlet, the tapered bore extending from the inlet;
    a conduit connecting the inlet to the outlet enabling fluid flow from the inlet to the outlet;
    a normally open slotted and compressible head for sealing the inlet, the head being movably disposed between a position in sealing engagement with the inlet, wherein the inlet completely closes the slot, and a position within the tapered bore out of sealing engagement with the inlet; and
    a flexible body depending from the head;
    wherein the slot of the head opens as the head is moved from the inlet to the tapered bore by a member external to the flow control device which engages the head and depresses the head into the tapered bore, opening the slot; and
    the flexible body comprises outwardly tapered and slotted side walls forming legs which are flexed as the head is moved from the inlet to the tapered bore, providing a return force for returning the head to the position sealing the inlet when the external member is removed.

15. The flow control device of claim 14,
    wherein the valve body further defines a second bore having a straight wall extending from the tapered bore;

a third bore extending from the second bore, the third bore having a rectangular cross section as viewed along a longitudinal axis of the flow control device; and a well connected to the third bore, wherein the outlet extends from the well;

wherein the flexible body has a first end connected to the head, a second end, and a base connected to the elongated legs at the second end of the flexible body, the base being rectangular as viewed along the longitudinal axis, and the base sits in the well, the movable head being movable from the position in sealing engagement with the inlet, through the tapered bore into the second bore, the slot being completely opened when the head is in the second bore.

16. A control device comprising:

an inlet;

an outlet;

an conduit connecting the inlet to the outlet enabling fluid flow from the inlet to the outlet;

a normally open slotted and compressible head movably disposed between the inlet and the outlet, wherein the inlet closes the slot when the head is in a position in sealing engagement with the inlet, and the slot is opened when the head is moved out of sealing engagement with the inlet, allowing fluid to flow through the conduit; and a spring coupled to the head, biasing the head towards the inlet;

wherein the head is movable by a force from the position in sealing engagement with the inlet to a position opening the inlet and removal of the force causes the spring to return the head to its position in sealing engagement with the inlet.

17. The flow control device of claim 12, wherein the conduit is defined by the head and extends from the head to the outlet.

18. The flow control device of claim 16, wherein the inlet and the outlet are defined by a valve body, the valve body further defining a tapered bore extending from and being inwardly tapered towards the inlet, wherein the slot opens as the head is moved into the tapered bore.

19. A flow control device comprising:

an inlet;

an outlet;

a conduit connecting the inlet to the outlet enabling fluid flow from the inlet to the outlet;

a normally open slotted and compressible head for sealing the inlet, the head being movably disposed between a position sealing the inlet and a non-sealing position, the inlet closing the slot when the head is in the position sealing the inlet, the head having an outer peripheral surface with longitudinally extending grooves; and a flexible body depending from the head, the flexible body providing a return force for returning the head to the position sealing the inlet when the head is moved to the non-sealing position;

wherein the slot of the head is in the form of a multi-sided geometric figure with opened segments when the head is in the non-sealing position.

20. The flow control device of claim 19, wherein the inlet and the outlet are defined by a valve body, the valve body further defining a tapered bore extending from and being inwardly tapered towards the inlet, wherein the slot opens as the head is moved into the tapered bore.

21. A method of fabricating a flow control device comprising:

(a) molding an inlet member having an axis of flow, an inlet, a coaxial seat beyond the inlet, and an expansion chamber beyond the coaxial seat;

(b) molding an outlet member which complements the inlet member and has a coaxial support;

(c) inserting an expandable control member, having, before insertion, a normally open slot into the inlet member with respect to the seat such that said inlet closes the slot; and (d) joining the outlet member to the inlet member with the control member therein and the slot closed.

22. The method of claim 21, comprising molding the control member of an elastomeric material with the normally open slot extending therethrough.

23. The method of claim 21, further comprising molding the control member of an elastomeric material with an inner cylindrical shell extending from the open slot for movement into an outlet when the control member is depressed.

24. A valve comprising:

an inlet;

an outlet;

a conduit connecting the inlet to the outlet to enable fluid flow from the inlet to the outlet;

a normally open slotted and compressible head movably disposed between the inlet and the outlet, wherein the inlet closes the slot when the head is within the inlet, sealing the inlet, and the slot is opened when the head is moved out of the inlet, allowing fluid to flow through the conduit; and resilient means for providing a force on the head towards the inlet.

25. The valve of claim 24, further comprising a valve body defining the inlet, the outlet and at least a portion of the conduit, wherein the valve body has an exterior surface including at least one flat wall.

26. The valve of claim 26, wherein a portion of the exterior surface includes four flat walls connected to form a rectangle.

27. A valve for controlling fluid flow comprising:

a valve body defining a bore extending therethrough, the bore having a first portion defining an inlet to the valve body and a second portion defining an outlet to the valve body;

a conduit connecting the inlet to the outlet: and a flexible member disposed within the valve body, the flexible member defining, at least in part, the conduit between the inlet and the outlet, the flexible member comprising:

a movable head having a normally open slot therethrough, the movable head being movably disposed within the valve body between positions within and outside of the first portion, wherein the first portion closes the slot, sealing the inlet, and the slot opens as the head is moved outside of the first portion, allowing fluid to flow through the slot and conduit to the outlet; and a flexible body portion extending from the head, the flexible body portion providing a force on the head towards the inlet.

28. The valve of claim 27, wherein the valve body further defines a third portion extending from the first portion, the third portion being inwardly tapered toward the first portion, wherein the slot opens as the head is moved into the third portion.

29. The valve of claim 28, further comprising a fourth portion with a straight wall, the fourth portion being between the third portion and the second portion, wherein the slot is completely opened when the head is moved into the fourth portion.

30. The valve of claim 29, wherein the conduit is further defined, at least in part, by the valve body.

31. The valve of claim 29, wherein the conduit is defined, at least in part, by the movable head.

32. The valve of claim 31, wherein the conduit is further defined, at least in part, by the flexible body.

33. The valve of claim 32, wherein the conduit is further defined, at least in part, by the valve body.

34. The valve of claim 29, wherein the valve body has an axis extending through the inlet and the outlet and the bore has a fourth portion extending parallel to the axis of the valve body and a base, wherein the flexible body portion has an end bearing against the base.

35. A flow control device comprising:
   a valve body defining an inlet, an outlet, a tapered bore between the inlet and the outlet, the tapered bore being inwardly tapered towards the inlet, and a straight walled bore between the tapered bore and the outlet; and
   a flexible member comprising a head portion movably disposed within the valve body, the head portion having a normally opened slot extending therethrough, and a flexible body portion extending from the head portion, the flexible body portion providing a force on the head towards the inlet;
   wherein the inlet closes the slot when the head portion is within the inlet and the slot opens as the head portion is moved from the inlet into the tapered bore, allowing fluid to flow from the inlet to the outlet, the slot opening completely when the head is moved into the straight walled bore.

36. The control device of claim 35, wherein the flexible member defines, at least in part, a conduit between the inlet and the outlet for the flow of fluid when the slot is open.

37. A flow control device for activation by a tip of a male luer taper, comprising:
   a valve body having an internal surface defining an opening within and extending through the valve body, the internal surface having a first portion defining an entrance to the valve body, a second portion, and a third portion defining an outlet of the valve body, the second portion being located between the first and third portions and the first portion being adapted to receive a male luer taper, the internal surface further defining a base portion between the second and third portions, the base portion extending toward a longitudinal axis through the center of the valve body; and
   a flexible member disposed within the opening, the flexible member defining, at least in part, a channel for fluid flow from the entrance to the outlet, the flexible member comprising:
      a slidable, movable compressible head having an external surface portion substantially perpendicular to the longitudinal axis,
      internal side walls extending through a central portion of the head and the external surface portion, the internal side walls being connected along edges parallel to the longitudinal axis of the device, the external surface portion and the internal side walls defining a normally open and bounded passage extending through the central portion of the head and the external surface,
      the movable head being slidably disposed within the opening between the first and second portions of the internal surface of the valve body,
      the first portion of the valve body and the head being dimensioned such that when the head is within the first portion, the first portion compresses the head, bringing at least a portion of the side walls of the normally open and bounded passage into contact with each other, closing the passage and sealing the entrance, and the second portion of the valve body being dimensioned larger than the first portion to allow the head to expand sufficiently for the passage to open when the head is moved from the first portion to the second portion by the tip of the male luer taper, allowing fluid to flow through the passage and channel to the outlet; and
      a flexible body portion extending from the head toward the outlet, the flexible body portion having an end opposite the head, the end of the flexible body portion being supported by the base portion of the valve body, the flexible body portion being compressed as the head is moved from the first portion to the second portion to provide a force on the head to return the head to the entrance when the male luer taper is removed from the entrance.

38. The flow control device of claim 37, wherein the valve body has an exterior surface portion around the entrance, substantially perpendicular to the longitudinal axis of the device, and the external surface portion of the head is proximate the exterior surface portion of the valve body when the head is sealing the entrance, prior to activation.

39. The flow control device of claim 38, wherein the internal surface of the valve body defines a tapered portion connecting the first and second portions, the tapered portion being outwardly tapered toward the second portion.

40. The flow control device of claim 39, wherein the head has an exterior wall extending from the external surface portion of the head to the flexible body portion and the internal surface of the valve body is dimensioned such that as the head is moved from the first portion to the second portion by the tip of the male luer taper, the exterior wall of the head is in continuous contact with the internal surface of the valve body, providing a seal between the exterior wall of the head and the internal surface of the valve body.

41. The flow control device of claim 37, wherein the internal side walls and exterior surface of the head form a star-shaped geometric figure when the head is in the second portion and the normally open and bounded passage is open.

42. The flow control device of claim 37, wherein the flexible body portion comprises walls which flex outwardly when the head is moved from the first portion to the second portion, to provide the return force on the head.

43. The flow control device of claim 37, wherein the flexible body portion includes a spring for providing the return force on the head.

44. The flow control device of claim 43, wherein the flexible body portion defines an inner flow passage extending continuously from the normally open and bounded passage through the head to the outlet.

45. The flow control device of claim 37, wherein the head has a round cross-section.

46. A method of controlling fluid in a flow control device including an entrance, an outlet, a compressible head having a normally open and bounded passage extending therethrough, the passage of the head being defined by an external surface portion of the head and internal side walls extending through a central portion of the head and the external surface, the internal side walls being connected along edges parallel to a longitudinal axis of the flow control device, and a flexible body extending from the head towards the outlet, the method comprising:

compressing the head by the entrance to close the passage by bringing at least a portion of the side walls of the passage into contact with each other, preventing fluid flow through the entrance;

inserting a male luer taper into the entrance of the valve body to engage an outer portion of the external surface of the head around the closed passage by the tip of the male luer taper;

continuing insertion of the male luer taper into the entrance to slidably depress the head toward the outlet, into a portion of the flow control device dimensioned larger than the entrance, to reduce the compression of the head, opening the passage and permitting fluid flow through the passage and flow control device;

compressing the flexible body as the head is slidably depressed, thereby increasing a return force on the head toward the entrance;

removing the male luer taper from the entrance;

returning the head to the entrance by the return force; and compressing the head by the entrance to close the passage, sealing the entrance.

47. The method of claim 46 wherein the valve body comprises an external surface surrounding the entrance, the method further comprising returning the head to the entrance such that the external surface of the head is proximate the external surface of the valve body surrounding the entrance.

* * * * *

UNITED STATES PATENT AND TRADEMARK OFFICE
CERTIFICATE OF CORRECTION

PATENT NO. : 6,068,011
DATED : May 30, 2000
INVENTOR(S) : JOSEPH R. PARADIS

It is certified that error appears in the above-identified patent and that said Letters Patent is hereby corrected as shown below:

Column 7, claim 3, line 5, after "outlet", insert a comma --,--.

Column 8, claim 9, line 8, change "inlets" to --inlet,--.

Column 10, claim 22, line 1, after "21," and before "comprising" insert --further--.

Column 10, claim 26, line 1, change "26" to --25--.

Signed and Sealed this

Seventeenth Day of April, 2001

*Attest:*

NICHOLAS P. GODICI

*Attesting Officer*   Acting Director of the United States Patent and Trademark Office